(12) United States Patent  
Becker

(10) Patent No.: US 11,950,996 B2  
(45) Date of Patent: Apr. 9, 2024

(54) HYBRID BREAST IMPLANT, METHOD FOR MAKING AND USING SAME

(71) Applicant: Hilton Becker, Boca Raton, FL (US)

(72) Inventor: Hilton Becker, Boca Raton, FL (US)

( * ) Notice: Subject to any disclaimer, the term of this patent is extended or adjusted under 35 U.S.C. 154(b) by 1578 days.

(21) Appl. No.: 16/154,066

(22) Filed: Oct. 8, 2018

(65) Prior Publication Data

US 2019/0038397 A1 Feb. 7, 2019

Related U.S. Application Data

(63) Continuation of application No. 14/711,722, filed on May 13, 2015, now Pat. No. 10,123,868.

(51) Int. Cl.
*A61F 2/12* (2006.01)
*A61F 2/00* (2006.01)
*A61F 2/30* (2006.01)

(52) U.S. Cl.
CPC .............. *A61F 2/12* (2013.01); *A61F 2/0059* (2013.01); *A61F 2002/30242* (2013.01); *A61F 2002/30593* (2013.01); *A61F 2210/0057* (2013.01); *A61F 2210/0061* (2013.01); *A61F 2230/0071* (2013.01); *A61F 2230/0076* (2013.01); *A61F 2240/001* (2013.01); *A61F 2250/0003* (2013.01)

(58) Field of Classification Search
CPC ....................... A61F 2/12; A61F 2/0059; A61F 2002/30593; A61F 2210/0057; A61F 2230/0071; A61F 2250/0003; A61F 2/0095

See application file for complete search history.

(56) References Cited

U.S. PATENT DOCUMENTS

| | | | | | |
|---|---|---|---|---|---|
| 3,663,968 | A | * | 5/1972 | Mohl | A61F 2/52 623/7 |
| 3,852,833 | A | * | 12/1974 | Koneke | A61F 2/52 623/7 |
| 3,934,274 | A | * | 1/1976 | Hartley, Jr. | A61F 2/12 450/38 |
| 4,298,998 | A | * | 11/1981 | Naficy | A61L 27/18 623/8 |
| 4,428,082 | A | * | 1/1984 | Naficy | A61F 2/12 623/8 |

(Continued)

*Primary Examiner* — Seema Mathew
(74) *Attorney, Agent, or Firm* — Weiss & Moy, PC; Jeffrey D. Moy

(57) ABSTRACT

An implant includes: a sinusoidal container that includes: a plurality of projections; a plurality of troughs; and a plurality of smooth interfaces, wherein a smooth interface is interposed between a projection and an adjacent trough for the plurality of projections, troughs, and interfaces to provide a smooth continuous transition between adjacent projections and troughs. A process for making an implant includes: forming a sinusoidal container from a polymer, the sinusoidal container including: a plurality of projections; a plurality of troughs; and a plurality of smooth interfaces, wherein a smooth interface is interposed between a projection and an adjacent trough for the plurality of projections, troughs, and interfaces to provide a smooth continuous transition between adjacent projections and troughs; and providing a filling tube attached to the sinusoidal container to make the implant.

12 Claims, 30 Drawing Sheets

(56) References Cited

U.S. PATENT DOCUMENTS

| | | | | |
|---|---|---|---|---|
| 4,433,440 A * | 2/1984 | Cohen | A61F 2/12 | 623/8 |
| 4,531,244 A * | 7/1985 | Hamas | A61F 2/12 | 623/8 |
| 4,605,412 A * | 8/1986 | LaForest | A61F 2/12 | 623/8 |
| 4,650,487 A * | 3/1987 | Chaglassian | A61F 2/12 | 623/8 |
| 4,773,909 A * | 9/1988 | Chaglassian | A61F 2/12 | 623/7 |
| 4,790,848 A * | 12/1988 | Cronin | A61F 2/12 | 623/8 |
| 4,944,749 A * | 7/1990 | Becker | A61F 2/12 | 623/8 |
| 4,955,907 A * | 9/1990 | Ledergerber | A61L 27/34 | 623/8 |
| 4,969,899 A * | 11/1990 | Cox, Jr. | A61F 2/12 | 623/8 |
| 5,383,929 A * | 1/1995 | Ledergerber | A61L 27/34 | 623/8 |
| 5,447,535 A * | 9/1995 | Muller | A61F 2/12 | 623/8 |
| 5,496,367 A * | 3/1996 | Fisher | A61F 2/12 | 623/8 |
| 5,496,370 A * | 3/1996 | Hamas | A61F 2/02 | 623/8 |
| 5,549,671 A * | 8/1996 | Waybright | A61F 2/12 | 623/7 |
| 5,571,179 A * | 11/1996 | Manders | A61B 90/02 | 623/8 |
| 5,779,734 A * | 7/1998 | Ledergerber | A61F 2/12 | 623/8 |
| 5,843,189 A * | 12/1998 | Perouse | A61F 2/12 | 623/7 |
| 5,902,335 A * | 5/1999 | Snyder, Jr. | A61F 2/52 | 623/7 |
| 6,146,418 A * | 11/2000 | Berman | A61M 31/00 | 623/7 |
| 6,290,708 B1 * | 9/2001 | Kugel | A61F 2/0063 | 602/44 |
| 6,520,989 B1 * | 2/2003 | Eaton | A61F 2/52 | 623/7 |
| 6,605,116 B2 * | 8/2003 | Falcon | A61F 2/12 | 156/219 |
| 6,802,861 B1 * | 10/2004 | Hamas | A61F 2/12 | 623/7 |
| 7,988,731 B2 * | 8/2011 | Govrin-Yehudian | A61F 2/12 | 623/7 |
| 8,092,527 B2 * | 1/2012 | Brennan | A61F 2/12 | 623/8 |
| 8,202,316 B2 * | 6/2012 | Ledergerber | A61F 2/12 | 623/8 |
| 8,556,968 B2 * | 10/2013 | Hamas | A61F 2/12 | 623/8 |
| 8,871,129 B2 * | 10/2014 | Mojaradi | A61F 2/12 | 623/8 |
| 9,486,309 B2 * | 11/2016 | Schuessler | A61F 2/12 | |
| 9,579,077 B2 * | 2/2017 | Casanova | A61B 90/39 | |
| 10,052,190 B2 * | 8/2018 | Chitre | A61B 90/02 | |
| 10,583,016 B2 * | 3/2020 | Valdiserra | A61F 2/5046 | |
| 11,571,271 B2 * | 2/2023 | Martinez | A61F 2/12 | |
| 2009/0198329 A1 * | 8/2009 | Kesten | A61F 2/12 | 623/8 |
| 2010/0114311 A1 * | 5/2010 | Becker | A61F 2/12 | 623/8 |
| 2012/0277860 A1 * | 11/2012 | Dvir | A61L 27/446 | 427/2.24 |
| 2014/0135924 A1 * | 5/2014 | Renke | A61F 2/12 | 623/8 |
| 2015/0351900 A1 * | 12/2015 | Glicksman | A61B 90/94 | 623/8 |
| 2017/0039618 A1 * | 2/2017 | Bonacci | G05B 19/27 | |
| 2017/0348089 A1 * | 12/2017 | Becker | A61F 2/12 | |

* cited by examiner

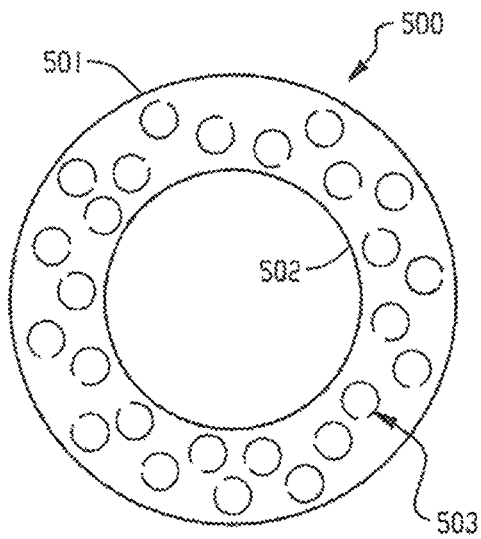 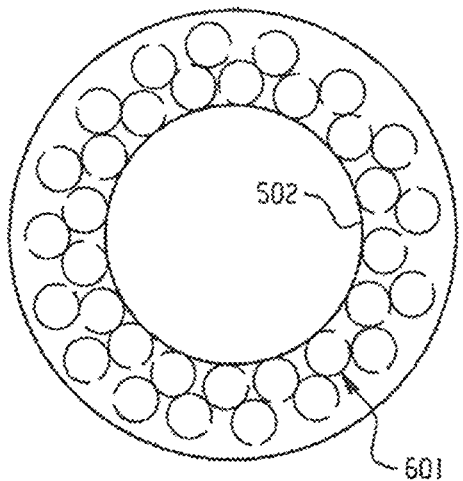
Fig. 5  Fig. 6
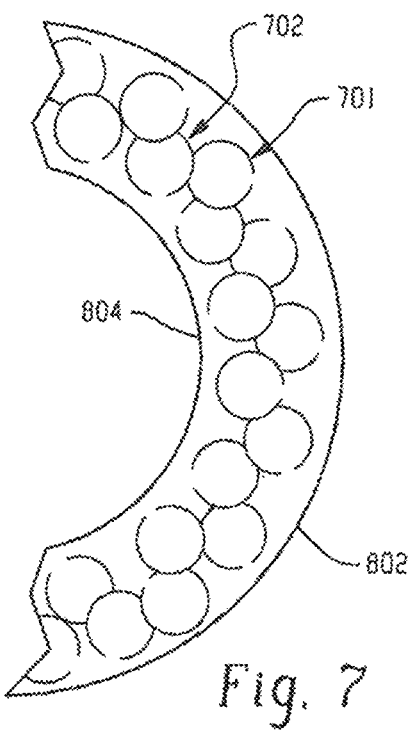 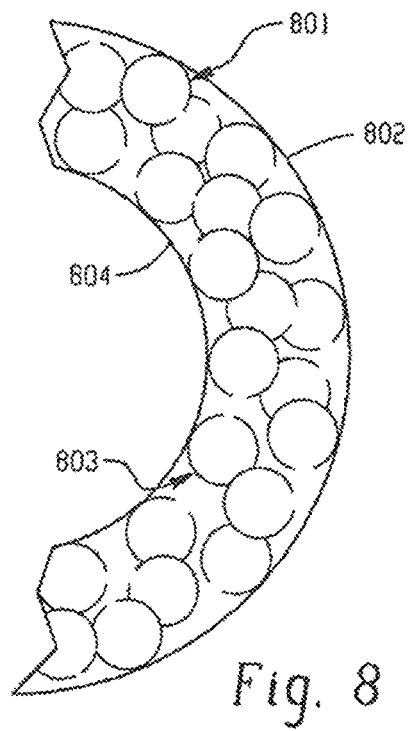
Fig. 7  Fig. 8

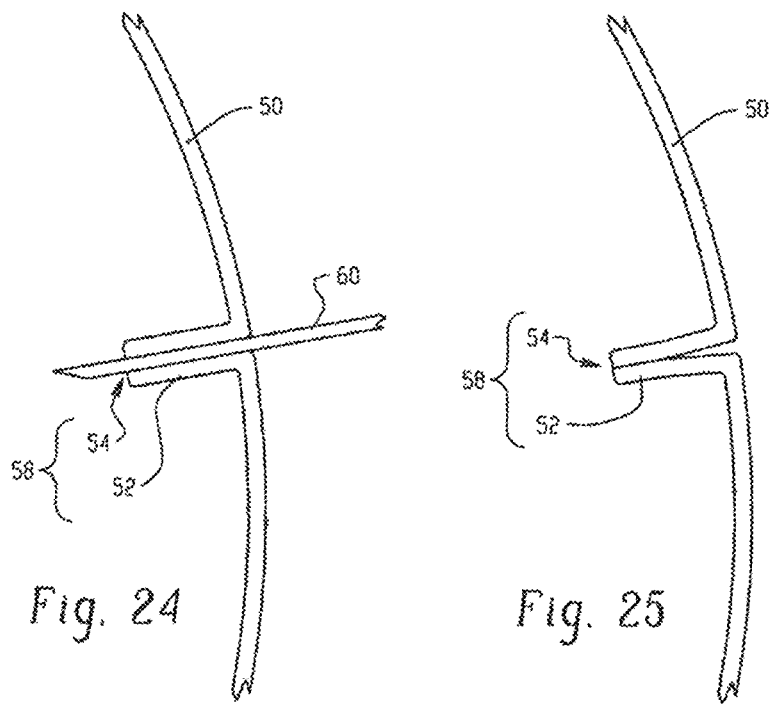
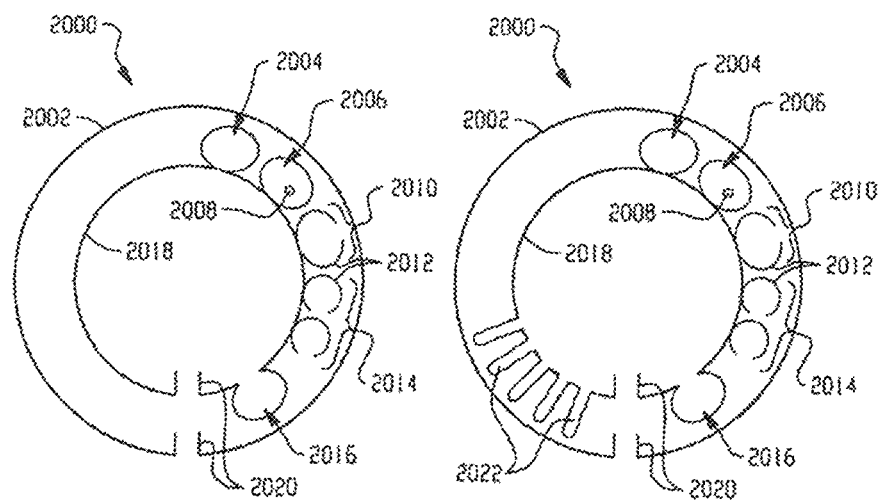

HYBRID BREAST IMPLANT, METHOD FOR MAKING AND USING SAME

CROSS REFERENCE TO RELATED APPLICATION

This application claims priority from U.S. Provisional Patent Application Ser. No. 62/079,531, filed Nov. 13, 2014, which is incorporated herein by reference in its entirety. This application is a continuation-in-part of U.S. application Ser. No. 13/961,348 filed Aug. 7, 2013, which is a continuation-in-part of International Application No. PCT/US2012/053334 filed Aug. 31, 2012, and U.S. patent application Ser. No. 13/598,723 filed Aug. 30, 2012, which both claim priority to U.S. Provisional Patent Application Ser. Nos. 61/671,992 filed Jul. 16, 2012, 61/602,300 filed Feb. 23, 2012, and 61/548,993 filed Oct. 19, 2011.

BACKGROUND

A breast implant is commonly used to correct shape or volume deformity of the breast due to breast removal following cancer or to correct size and asymmetry. Examples of breast implants available in the United States include silicone gel-filled implants and saline-filled implants. However, silicone gel-filled implants and saline-filled implants diverge from an ideal implant.

Relative to saline implants, silicone gel-filled implants can offer superior feel; however, silicone gel implants have a higher capsular contracture rate and should be removed if ruptured. Further, a 1992 United States Food and Drug Administration (FDA) moratorium on the use of silicone gel-filled implants negatively impacted the perception of their safety. Restraints on approval of silicone gel implant devices and alternative implant filling materials still exist.

Saline-filled implants (also referred to herein as saline implants) have been FDA approved and have an excellent safety record spanning 30 years. On the other hand, saline-filled implants may feel less natural than silicone gel implants, and surface rippling can be problematic. If a saline-filled implant leaks, the subject's body absorbs the saline, and the volume of the saline-filled implant decreases. The amount of saline leakage can be substantial, sometimes to the point of being substantially free of saline. In this circumstance, the empty or nearly empty shell can be removed and replaced.

Additionally, physicians temporarily use a tissue expander to stretch or facilitate growth of tissue in a patient. For example, a surgeon may place a tissue expander in a mastectomy patient as part of reconstructive repair of the tissue. Tissue expanders commonly contain the same filling fluid and suffer similar physical problems as, e.g., saline-filled implants.

Due to regulatory overview by the FDA, introducing a breast implant or tissue expander in the United States can be fraught with enormous expense of time and money due to compliance with FDA requirements, which can involve extensive clinical trials and reporting occurring over the course of years. Typically, review of previously unapproved materials in, for example, breast implants or tissue expanders can be a leading factor in the regulatory approval delay for these devices.

Materials and implants that overcome the above issues would be well-received by those skilled in the art.

SUMMARY

Disclosed herein is an implant comprising: a sinusoidal container that comprises: a plurality of projections; a plurality of troughs; and a plurality of smooth interfaces, wherein a smooth interface is interposed between a projection and an adjacent trough for the plurality of projections, troughs, and interfaces to provide a smooth continuous transition between adjacent projections and troughs.

Also disclosed is a process for making an implant, the process comprising: forming a sinusoidal container from a polymer, the sinusoidal container comprising: a plurality of projections; a plurality of troughs; and a plurality of smooth interfaces, wherein a smooth interface is interposed between a projection and an adjacent trough for the plurality of projections, troughs, and interfaces to provide a smooth continuous transition between adjacent projections and troughs; and providing a filling tube attached to the sinusoidal container to make the implant.

Further disclosed is a method for expanding tissue, the method comprising: disposing the implant of claim 1 in tissue; and filling the implant with a fluid to expand the tissue.

Additionally disclosed is an implant comprising: a first sinusoidal container that comprises: a plurality of projections; a plurality of troughs; and a plurality of smooth interfaces, wherein a smooth interface is interposed between a projection and an adjacent trough for the plurality of projections, troughs, and interfaces to provide a smooth continuous transition between adjacent projections and troughs in the first sinusoidal container; and a second sinusoidal container disposed in the first sinusoidal container, the second sinusoidal container comprising: a plurality of projections; a plurality of troughs; and a plurality of smooth interfaces, wherein a smooth interface is interposed between a projection and an adjacent trough for the plurality of projections, troughs, and interfaces to provide a smooth continuous transition between adjacent projections and troughs in the second sinusoidal container.

BRIEF DESCRIPTION OF THE DRAWINGS

The following descriptions should not be considered limiting in any way. With reference to the accompanying drawings, like elements are numbered alike:

FIG. 5 shows a cross-section of a breast implant having free-floating members interposed between an inner container and outer container;

FIG. 6 shows a cross-section of a breast implant having members attached to an inner container;

FIG. 7 shows a partial cross-section of a breast implant having members attached to other members;

FIG. 8 shows a cross-section of a breast implant having members attached to an inner container and outer container;

FIGS. 24 and 25 show cross-sections of a valve and needle for injection of a fluid into a breast implant;

FIG. 26 shows a cross-section of members disposed on an inner container of an implant;

FIG. 27 shows a cross-section of members disposed on an implant that has projections radially disposed on an inner container of the implant;

DETAILED DESCRIPTION

A detailed description of one or more embodiments of the disclosed apparatus and method are presented herein by way of exemplification and not limitation with reference to the Figures.

Disclosed herein is an implant such as a breast implant or other tissue implant such as a tissue expander that uses biologically compatible and safe materials. Such materials have gained approval from the United States Food and Drug Administration (FDA) as of the date of this application. An implant constructed of these materials has a feel that emulates that of biological tissue. It was discovered that a breast (or other tissue) implant or tissue expander herein that includes these biologically safe and compatible materials prevents surface rippling of the implant or tissue expander as well as obtains an effective fluid viscosity that mimics that of natural breast tissue. Additionally, the tissue expander when disposed in a patient provides a feel to the patient's breast that is substantially similar to natural, healthy breast tissue. Moreover, the tissue expander when disposed in a patient provides a look to the patient's breast that is substantially similar to natural, healthy breast tissue. Consequently, the tissue expander, although removable from the patient by, e.g., a surgeon, provides a substantially identical look, feel, and aesthetic presentation as natural, healthy human breast tissue. Further, the disclosed implant and tissue expander can be efficiently manufactured at a low relative cost. Moreover, the implant and tissue expander herein are volumetrically compressible. That is, the implant and tissue expander can be evacuated prior to implantation so that the implant or tissue expander can be implanted in a substantially fluid-free state or that partially contain a fluid (e.g., a liquid, solid, or gas). The compact size of the implant and tissue expander can thus eliminate pressure on a mastectomy incision and skin flaps. After implantation, the implant (or tissue expander) can be filled with a desired volume of fluid. Moreover, the implant (or tissue expander) can be adjusted to a suitable volume multiple times over the lifetime of the implant (or tissue expander). Hereinafter, use of the term "implant" refers to permanent, semi-permanent, or temporarily implanted articles such as the tissue expander. It is contemplated that the tissue expander is implanted in patient and subsequently removed from the patient after a selected period has passed. Such a period can be determined by factors that include, e.g., an amount of tissue expansion due to presence of the tissue expander in the patient, acquisition of a certain volumetric size of the tissue of interest (e.g., breast tissue), and the like. As used herein, when "implant" is recited, implant refers to a breast implant (or other temporary implant or permanent implant) or tissue expander.

Figures 1, 2:
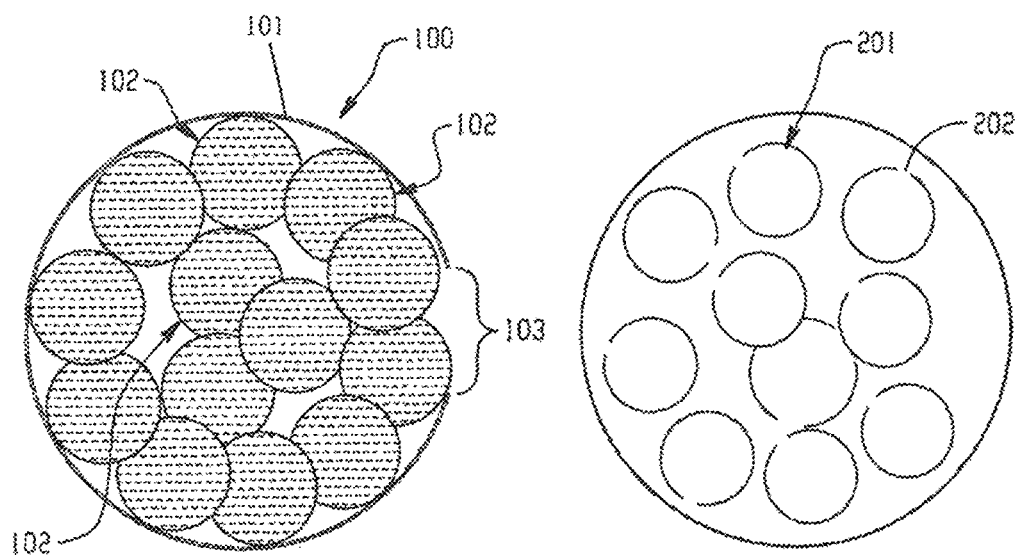
FIG. 1 shows a cross-section of a breast implant having free-floating closed members.
FIG. 2 shows a cross-section of a breast implant having free-floating open members.

As shown in FIG. 1, in an embodiment, implant 100 includes outer container 101 and member 102 disposed in outer container 101. Particularly, a plurality of members 102 can be disposed in outer container 101. The surface of member 102 can be closed as shown in FIG. 1; such member 102 can be referred to as a closed member. Alternatively, the surface of member 201 can be open as shown in FIG. 2; such member 201 can be referred to as an open member. In another embodiment, implant 100 can contain a combination of a closed member 102 and an open member 201. As will be discussed more fully below, aperture 202 in open member 201 allows a fluid to flow in or out of open member 201 and can decrease motional perturbations of implant 100. Additionally, closed members 102 can also impede fluid flow. In this manner, motion of the fluid in an implant herein behaves similar to natural, healthy breast tissue. Aperture 202 can allow fluid communication from the exterior of member 201 to the interior of member 201. In some embodiments, members 102 and 201 can be free-floating in outer container 101. As used herein, "free-floating" refers to a member unattached to a surface of a container (e.g., an outer container or inner container). According to an embodiment, outer container 101 includes opening 103. Opening 103 is sealed with a patch having a valve once the members have been disposed. Members 102 or 201 can be inserted inside outer container 101 through opening 103, or outer container 101 can be formed around members 101 or 201. Unless otherwise specified or indicated, when "member" is used for the remainder of this document, "member" includes both open members 102 and closed members 201.

The pressure of closed members 102 can be different than the pressure of outer container 101. Consequently, depending on the wall thickness of closed members 102 and outer container 101, closed members 102 can have a higher compressibility than outer container 101. Alternatively, outer container 101 can be more compressible than closed members 102. Thus, closed members 102 can feel harder than outer container 101, or outer container 101 can feel harder than closed members 102. As a result, the overall tactile feel and appearance of implant 100 can obtain a desired rigidity, projection, and surface morphology by selection of the relative pressure and compressibility of closed members 101 and outer container 101.

Figures 3, 4:
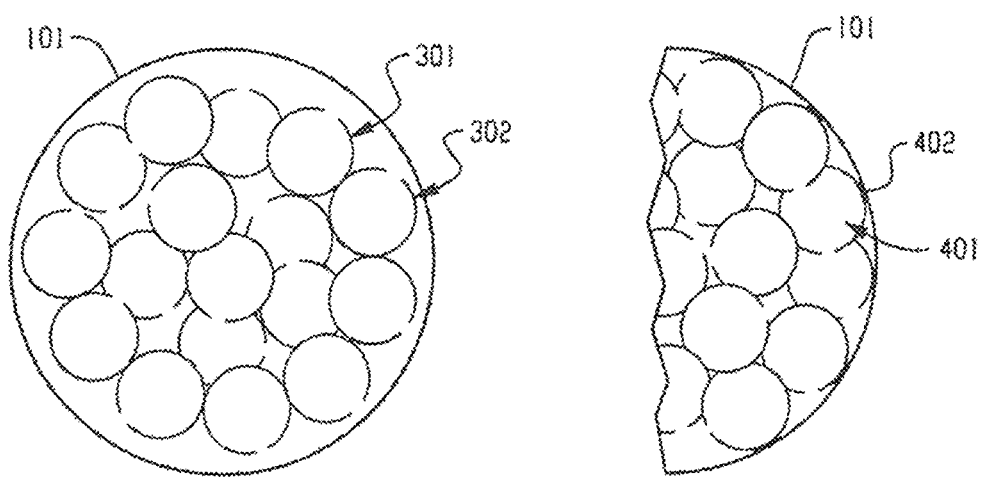
FIG. 3 shows a cross-section of a breast implant having open members attached to other members.
FIG. 4 shows a cross-section of a breast implant having members attached to a container.

In certain embodiments, members 102, 201 can be attached to various objects of implant 100. In an embodiment, member 301 is attached to another member 302 and disposed in outer container 101 as in FIG. 3. Some of members 301, 302 can be attached to each other to form a mass that includes a plurality of attached members. In another embodiment, a member can be detached from any other member. In a further embodiment, a plurality of masses of attached members (i.e., multiple groups of masses that are not connected to one another) can be disposed in outer container 101. FIG. 4 shows an embodiment where member 401 is attached to outer container 101 by attachment 402. In an additional embodiment, members 401 can be attached to themselves and to outer container 101.

As shown in FIG. 5, implant 500 includes outer container 501 and inner container 502 disposed in outer container 501. Member 503 can be interposed between inner container 502 and outer container 501. Member 503 can be detached from other items or can be attached to another other item of implant 500. In an embodiment, member 601 is attached to inner container 502 (FIG. 6). As shown in FIG. 7, member 701 can be attached to another member 702 between inner container 804 and outer container 802. In an embodiment, member 801 can be attached to outer container 802, and member 803 can be attached to inner container 804. According to yet another embodiment, a member can be attached to the outer container, the inner container, another member, or a combination comprising at least one of the foregoing. In an alternative embodiment, a member is unattached to (i.e., detached from) the outer container, the inner container, another member, or a combination comprising at least one of the foregoing.

In a further embodiment, a member can be disposed in the inner container either attached or detached to another item including the inner surface of the inner container. In addition, a member can be interposed between the outer container and the inner container, and a member can be disposed in the inner container.

Figure 9:
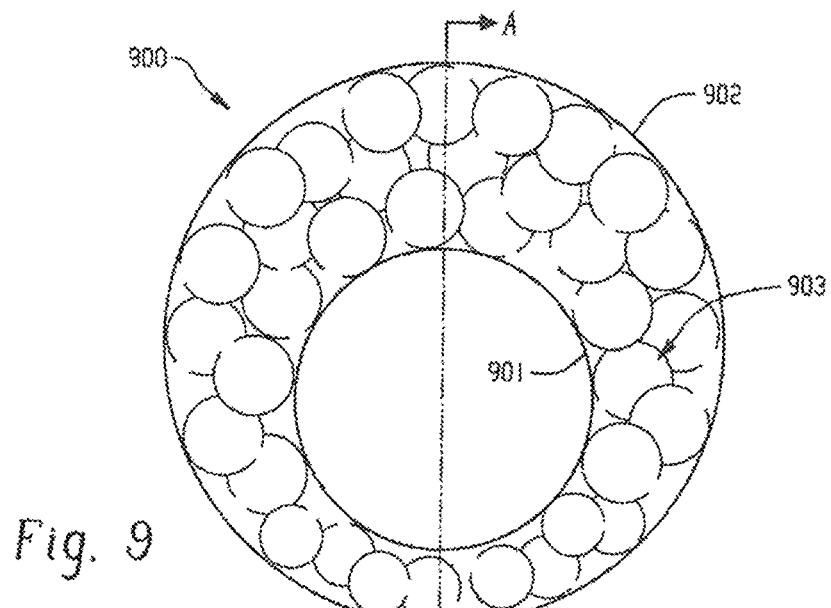
FIG. 9 shows a cross-section of a breast implant having an anatomical shape with an inner container disposed closer to an inferior portion of an outer container.
Figure 10:
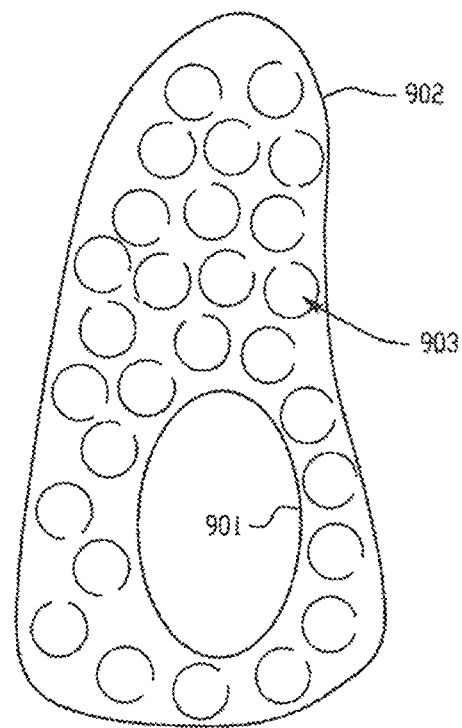
FIG. 10 shows a cross-section of a breast implant having an anatomical shape with an inner container disposed closer to an inferior portion of an outer container.

As in FIG. 9, the implant can have an anatomical shape, for example, a shape of a human breast. To achieve the anatomical shape, inner container 901 can be disposed proximate (i.e., in closer proximity) to the inferior portion of outer container 902 than the superior portion of outer container 902 as shown in the cross-sectional view from the ventral side of implant 900 in FIG. 9. Moreover, the number of members 903 interposed between outer container 902 and inner container 901 can be greater in the superior portion of outer container 902 than the inferior portion of outer container 902. In an embodiment, inner container 901 can be disposed proximate to the anterior portion of outer container 902 and further from the posterior portion of outer container 902 as shown in FIG. 10, which is a cross-section along line A-A of the implant 900 in FIG. 9. Other positions of inner container 901 within outer container 902 are contemplated to produce a shape of the implant in an anatomical shape. The position of inner container 901 can be determined by the number of members 903 in a region between inner container 901 and outer container 902.

Figure 11:
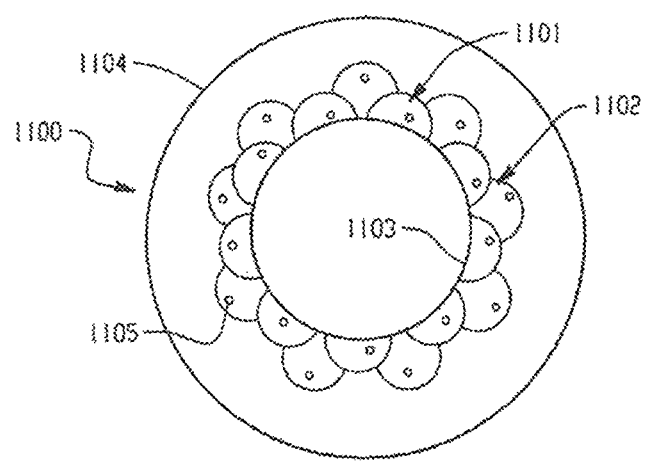
FIG. 11 shows a cross-section of a breast implant having semi-shell members attached in layers to an inner container.
Figure 12:
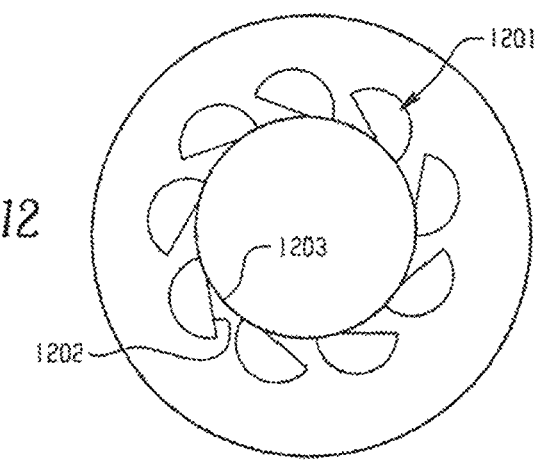
FIGS. 12 and 13 show cross-sections of a breast implant having semi-shell members partially attached to an inner container.
Figure 13:
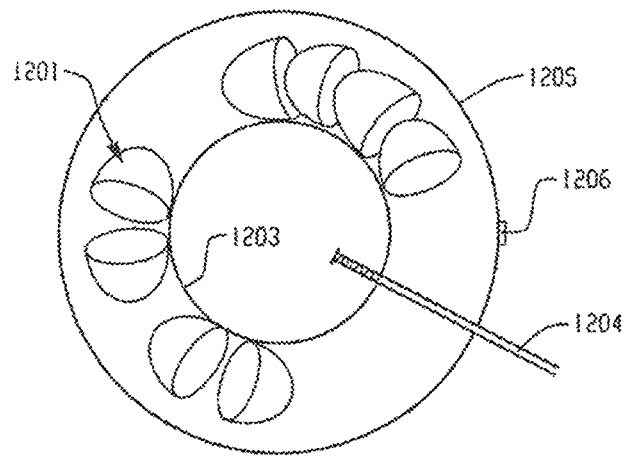

The shape of a member can vary and can be any shape that provides an obstruction to abrupt fluid flow in the implant. In an embodiment, the cross-sectional shape of a member is circular, ellipsoidal, crescent, irregular, cubic, tetrahedral, conical, a truncated version thereof, or a combination thereof. According to an embodiment, the members are semi-shells. Semi-shells can have a portion of the surface missing from a closed member or open member, and semi-shells are not merely a member with an opening for fluid flow as an opening is described herein. Exemplary semi-shells include hemispheres and other partial ellipsoids including partial spheroids and partial spheres and can also be partial cubes and tetrahedral or other multi-sided structures as well as cylindrical and tubular shapes and the like. In a non-limiting embodiment, as shown in FIG. 11, implant 1100 includes semi shell member 1101 attached to inner container 1103. Semi-shell 1101 has a base that can be fully attached to the inner container as in FIG. 11 or partially attached to inner container 1103 as in FIG. 12, which shows base 1202 of semi-shell 1201 partially detached from inner container 1203. With reference again to FIG. 11, semi-shell member 1101 can be disposed in a first layer on the surface of inner container 1103, and another semi shell member 1102 can be in a second layer that is disposed on the first layer. Semi-shell (1101 or 1102) can also have opening 1105. Although, openings (such as 1105 in FIG. 11) are not shown in FIG. 12, members 1201 can include an opening. As shown in FIG. 13, the placement of semi-shell members 1201 on inner container 1203 can be any configuration that allows fluid to bafflingly flow in outer container 1205. Semi-shell members 1201 can be disposed so that the closed portions of semi-shell members 1201 face one another or such that the closed portion faces an open portion of an adjacent semi-shell member 1201. The distance between adjacent semi-shell members 1201 can be any distance. In an embodiment, semi-shell members 1201 can be spaced apart so that they do not contact one another when the implant is filled with a fluid. In another embodiment, semi-shell members 1201 can be spaced apart so that they contact one another when the implant is filled with a fluid. In a further embodiment, semi-shell members 1201 can be spaced apart so that adjacent semi-shell members can be nested such that a portion of their walls overlap. FIG. 13 also shows filling tube 1204 through which a fluid can be disposed in inner container 1203. Patch 1206 is disposed on and seals outer container 1205. Patch 1206 covers an aperture that is used to fill outer container 1205 with a fluid.

The size of a member is about 1 millimeter (mm) to about 70 mm, specifically about 5 mm to about 60 mm, and more specifically about 10 mm to about 50 mm. As used herein, the "size of a member" refers to the greatest linear dimension of the member. According to an embodiment, different sizes of members are used inside the implant, or the size of the members are substantially the same. As used herein, "substantially the same" refers to a tolerance of 5%. When different sizes of members are used, the members may pack at a higher number density (relative to a uniform size of members being used) inside the implant with smaller members filling gaps between larger members.

In an embodiment, a member includes a wall and a void disposed within each member such that each member is hollow. In another embodiment, a member is a solid without a void. A member can contain pores disposed in the wall or solid portion thereof. The pores can be connected or detached from one another. In an embodiment, the member has open cell pores to communicate fluid through the pores. In some embodiments, the member has closed cell pores that can provide a spring-like restoring force if the member is compressed and then decompressed due to a fluid (liquid, gas, or solid) inside the closed pores. In a non-limiting embodiment, the member is an FDA-approved testicular implant. Such testicular implants have an outer elastomeric shell (e.g., silicone) and are filled with a fluid (e.g., saline).

The wall thickness of the member can be from about 228 micrometers (μm) (0.009 inches (in.)) to about 535 μm (0.021 in.), and specifically about 254 μm (0.010 in.) to about 457 μm (0.018 in.). In some embodiments, the wall thickness can be that of an FDA approved testicular implant or saline-filled breast implant. Moreover, the wall thickness in a member can be different at different regions of the member. In an embodiment, the member can have an ellipsoidal shape with the wall thickness being thicker at the ends of the ellipsoid and thinner in the middle region of the ellipsoid or have any variation of wall thickness throughout the member.

According to an embodiment, the member has an opening. The opening can be any shape (e.g., round, ellipsoidal, polygonal, and the like) and any size to allow fluid to pass into or out of the member from a container within which it is disposed (e.g., an outer container or inner container in an embodiment where the member is respectively disposed in the outer or inner container). The opening can have a size from about 0.01 mm (e.g., a substantially linear slit in the member) to about 10 mm, and specifically about 0.01 mm to about 4 mm. Here, "size" refers to the largest linear dimension of the opening, which can be any shape, e.g., circular, ellipsoidal, polygonal. The member can have more than one opening. Exemplary members have one opening, two openings, and the like. An upper limit to the number of openings is not limited as long as the member remains operable to baffle fluid flow in the implant. In an embodiment, the number of openings is less than 1000, specifically less than 50, and more specifically less than 10. In another embodiment, a member is closed and free of an opening that allows fluid communication from the exterior of the member to the interior of the member. Instead of having fluid communicate through the closed member, the closed member can be solid or have a void. The void in the closed member can be filled with a fluid, for example, saline, silicone gel, or other fluids described herein and those known in the art. In another embodiment, an implant includes an open member, a closed member, or a combination comprising at least one of the foregoing.

As discussed above, a member can be attached to the outer container, inner container, another member, or a combination comprising at least one of the foregoing. The attachment can be an adhesive (e.g., a biocompatible adhesive such as silicone glue), a physical attachment (such as a polymeric tether, suture, clip, and the like), or a combination comprising at least one of the foregoing. Additionally, instead of individual members being attached to each other or the inner or outer container, the member can be manufactured as a single aggregate of members, or the inner or outer container having members attached thereto can be manufactured as a single item. In an embodiment, members attached to one another can be attached in various geometric patterns. In particular, a plurality of members can be connected in a honeycomb shape. The honeycomb of members can be attached to, for example, the inner container.

The members can be attached to the entire exterior surface of the inner container. In some embodiments, a portion of the surface of the inner container can be exposed and not attached to a member. Likewise, either a portion or the entire interior surface of the outer container can be attached to a member.

The number of members inside the outer container can be from one up to as many members as the volume of the outer container can hold without rupturing or adversely affecting the structural integrity of the outer container. For example, for a 300 cubic centimeter (cc) (300 milliliter (mL)) outer container, one to about 30 closed members each having a volume of about 10 cc (10 mL) can be disposed in the outer container. In an embodiment, the number of open members disposed in the outer shell can be greater than or equal to the number of closed members due to the ability of the open members to be compressed. In an embodiment, the outer container is flexible (as described below) and expandable such that the volume of the members disposed in the outer container is about 1 volume percent (vol %) to about 120 vol %, specifically about 25 vol % to about 110 vol %, more specifically about 50 vol % to about 90 vol %, based on the nascent volume of the outer container. As used herein, "nascent volume" refers to the volume of an object before stretching of the object occurs.

Although various figures herein show one inner container, the number of inner containers is not so limited. Moreover, multiple inner containers can be disposed in the outer container. In an embodiment, an inner container can be disposed in another inner container, to create nested inner containers. According to another embodiment, an outer container can include nested inner containers, a further inner container disposed external to the nested inner containers, and a member. In a further embodiment, the implant includes an outer container, an inner container disposed in the outer container, and no members. In some embodiments, the implant includes an outer container, a member disposed in the outer container, and no inner container. In certain embodiments, the implant includes only an outer container without any members and without an inner container disposed in the outer container.

In a non-limiting embodiment, the member is flexible so that the shape of the member under compression can change to accommodate forces exerted on the member or the outer container of the implant. Alternatively, the member can be relatively rigid so that the member provides structural integrity and support to the shape of the implant.

According to an embodiment, the outer container, inner container, and the member are a same or different material, and each can be a medical grade elastomer so that the outer container, inner container, and member are flexible, resilient, and biocompatible. Exemplary material for the outer container, inner container, and member include silicone or other relatively inert or biocompatible materials for soft tissue replacement, particularly vascular grafts, breast implants, or testicular implants. Additionally, the outer container, inner container, and member can be an elastomer such as polyisobutylene-based thermoplastic elastomer, poly(ethylene terephthalate) (PET), poly(tetrafluoroethylene) (PTFE), polypropylene (PP), polyurethane (PU), or a combination comprising at least one of the foregoing. Further, the elastomer can be a thermoplastic elastomeric biomaterial, for example, polystyrene-b-polyisobutylene-b-polystyrene (SIBS). In another embodiment, the outer container is an FDA approved saline breast implant. In yet another embodiment, the outer container is an FDA approved saline implant modified with the features as described herein, for example, having an opening for disposal of a member therein.

In an embodiment, a member is disposed in the outer container as a closed member. A member has a wall and an internal void. According to an embodiment, a fluid can be disposed in a closed member. This fluid can be introduced into the member through a perforation in the wall. A patch can seal the perforation on the surface of the member. According to an embodiment, the fluid is introduced into the member by inserting a filling tube or syringe needle into the wall, creating a perforation. In a member having an opening, the fluid can be disposed in the member via the opening, and the opening sealed such that flow does not flow from the interior to the exterior of the member. Alternatively, the member can be made with a perforation or a valve for disposing the fluid. The patch adheres to the surface of the member by an adhesive such as a silicone-based glue or other biocompatible sealant. The patch can be the same or different material as the member. Moreover, the pressure inside the member can vary depending on the amount of fluid disposed in the member. As a result the volume of fluid disposed in the member and the wall thickness, the flexibility and compressibility of the member are variable and can be selected based on the desired fluid properties and aesthetic preferences for the implant.

The outer container or inner container can include a valve (for filling such a container with a fluid) such as a valve that allows reversible insertion of a tube (e.g., a filling tube). The tube can extend from inside the container (inner or outer container) to outside the outer container. The end of the tube disposed in the container can be, for example, straight or tapered. The end of the tube external to the implant can have an injection port for introducing a fluid that flows through the tube into the outer or inner container. An exemplary valve includes those that are used in adjustable breast implants sold under the trade name Spectrum Implant and Becker 50-50 Implant available from Mentor Corp. In an embodiment of the implant having such a valve, the implant can be filled post-implantation at least up to one year before removal of the filling tube. After the filling tube is removed, the implant is sealed by the valve.

According to an embodiment, the implant includes the tube that is undetachably disposed on the implant so that the tube is permanently attached to the implant. Here, the tube and the implant are removed together as a single unit from a patient at some time subsequent to disposition in the patient. In this manner, the tube remains attached to the implant while the implant is disposed in the patient. Accordingly, the implant in this embodiment is regarded as a tissue expander.

The filling tube can be made of metal, non-metal, or a combination thereof, such as stainless steel or plastic. In an embodiment the filling tube has a blunt end so that the member or inner container is not damaged by the filling tube. Damage to the member or inner container can cause, for example, leakage or shape deformation. Alternatively, a blunt syringe needle can be used to introduce a fluid into the implant with due care so that the member or inner container is not damaged.

In a method of preparing an implant, an outer container can be provided. The outer container can be formed to have a filling tube. The outer container can be formed to have a valve and filling tube. The outer container can be formed to have a valve, filling tube, opening for disposal of a member or inner container, or a combination comprising at least one of the foregoing. According to an embodiment, an inner container can be provided and formed to have a valve, filling tube, or a combination comprising at least one of the foregoing.

In an embodiment, a process of making an implant includes disposing an elastomer on a mandrel. For example, the mandrel can be dipped in a liquid elastomer or a liquid elastomer can be coated on the mandrel. The elastomer is cured and removed from the mandrel to produce a member, outer container, or inner container. The mandrel can include protrusions that are not coated by the elastomer so that the cured elastomer has holes due to the protrusions. In some embodiments, the mandrel includes protrusions that are coated by the elastomer so that the cured elastomer has protrusions that project from its surfaces (e.g., similar to bubbles) due to the protrusions on the mandrel to form an outer container with a plurality of protrusions distributed on the surface of the outer container. As an alternative, the member can be cut to produce the openings in the member. In a further embodiment, the member is produced by extruding an elastomer using an appropriate die, or the member can be formed in a mold to produce solid or hollow members.

A member can be attached to another member via an adhesive and inserted into the outer container through the opening in the outer container. In another embodiment, a member can be attached to an inner container, which is inserted into the outer container. In yet another embodiment, a member can be inserted into the outer container and attached thereto. In a further embodiment, a member is a semi-shell, and the base of the member is attached to the inner container or the outer container either partially or completely. After disposal of the member or the inner container in the outer container, the opening of the outer container can be sealed, for example, with a patch.

In an embodiment, an inner container having a filling tube is disposed in the outer container and the filling tube is disposed through a valve that is disposed in the outer container so that the filling tube extends from the internal portion of the inner container, through the outer container, and external to the outer container for fluid communication with the inner container.

According to an embodiment, the implant is useful as a breast implant, including implantation as a tissue expander or for augmentation. A method of using the implant includes disposing the implant into a subject, and adjusting a volume of a fluid in the implant. The implant can include an outer container; an inner container disposed in the outer container, a member attached to the inner container, and a tube removably disposed in the inner container and extending from the inner container, through the outer container, and terminating outside of the body of the subject. Adjusting the volume comprises transmitting fluid, through the tube, among the inner container and a source external to the subject. After achieving a selected volume of the implant, the tube can be removed.

According to an embodiment, the implant is the breast implant that is used for implantation as a tissue expander. A method for expanding tissue with the implant (e.g., the tissue expander) includes disposing the implant in a subject and adjusting a volume of fluid in the implant. The implant can include an outer container and a tube attached (e.g., permanently attached) to the outer container such that the tube extends from inside the patient at a location of the implant and terminates outside of the body of the subject. The implant can optionally include an inner container disposed in the outer container, and optionally a member attached to the inner container. Adjusting the volume includes transmitting fluid, through the tube, among the inner container and a source external to the subject. After achieving a selected volume of the implant, the tube can be removed. It is contemplated that, in an embodiment, the outer container includes a plurality of projections that appear as smooth bubbles distributed over an external surface of the outer container and which is further described below with respect to FIGS. 65, 66, 67, 68, 69, 70, 71, 72, 73, 74, 73, 74, 75, 77, 79, 81, 83, 85, and 87.

In some embodiments, the implant is the tissue expander that has the outer container and the tube undetachably connected to the outer container. Here, adjusting the volume of the implant includes transmitting fluid through the tube and disposing the fluid in the outer container to achieve a selected volume of the implant. Additionally, fluid can be removed from the inner container via the tube. Moreover, according to this embodiment, the tube is not removed from the implant. Instead, after a tissue in which the implant is disposed has been modified to have increased to a selected size due to volumetric expansion of the implant, the implant including the two is removed from the patient.

Figure 14:
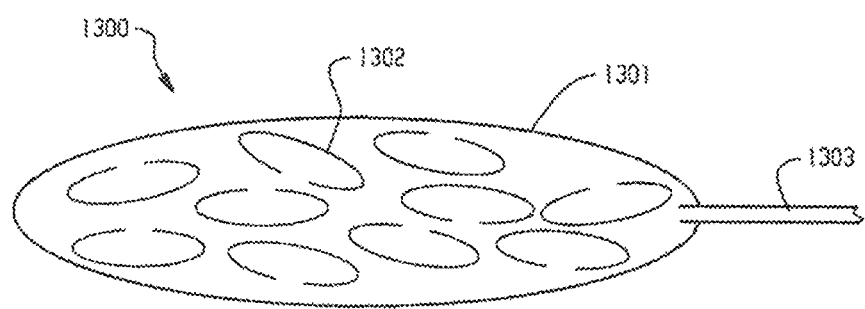
FIG. 14 shows a cross-section of a breast implant having free-floating open members after evacuation of air from the implant with an outer container and members collapsed.
Figure 16:
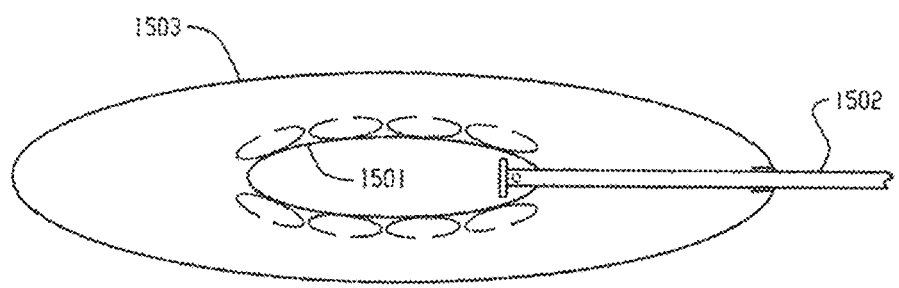
FIG. 16 shows a cross-section of a breast implant having open members attached to an inner container after evacuation of air from the inner container.

As shown in FIG. 14, to insert implant 1300 into the subject, implant 1300 having outer container 1301, members 1302, and filling tube 1303 can be evacuated through filling tube 1303 to compress outer container 1301 and members 1302. Such compression creates a smaller volume of implant 1300 to insert into the subject so that a smaller incision can be made to accommodate insertion of implant 1300 into the patient. Similarly, for an implant having an inner container, inner container 1501 can be evacuated through filling tube 1502, which extends from inside inner container 1501 to outside outer container 1503 as in FIG. 16.

The outer container, inner container, and member are flexible and elastic such that they can withstand compression and can be initially configured in an original shape. Upon compression, they obtain an intermediate shape in response to a compressive force. When the compressive force is released or through introduction of a fluid, they obtain a terminal shape in response to removal of the compressive force. The compressive force is, for example, due to evacuation such that the pressure inside the implant is below ambient pressure. The terminal shape can be that of or similar to the original shape. In an embodiment, upon removal of the compressive force, the members provide a restoring force to the implant so that the implant expands toward the terminal shape.

Figure 15:
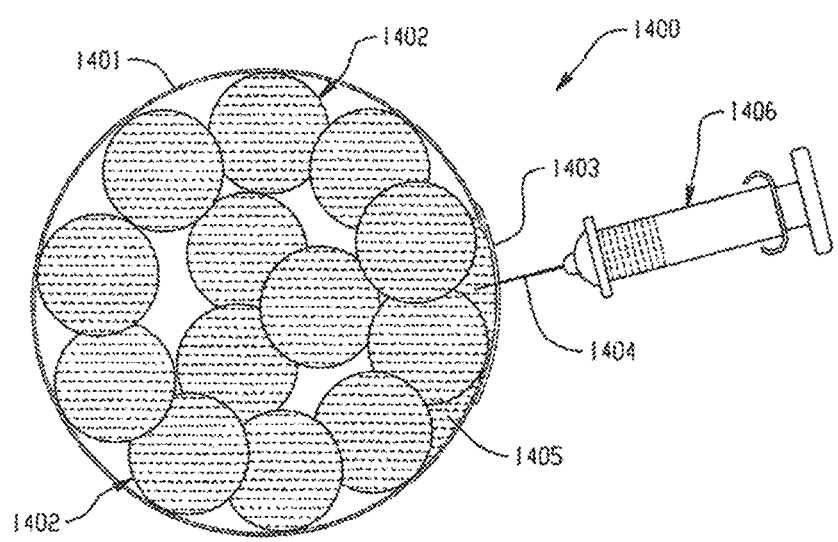
FIG. 15 shows a cross-section of a breast implant having free-floating closed members in response to introduction of a fluid.

The size of the implant is adjusted by introducing a fluid (e.g., saline) into the implant. In the implant shown in FIG. 14, a fluid is disposed in the outer container 1301 through a filling tube 1303 that also can be attached to an injection port (not shown) for later adjustment of the fluid. That is, in an embodiment, as shown in FIG. 15, the implant 1400 includes an outer container 1401 and members 1402. An opening in the outer container 1401 through which members 1402 are inserted into the outer container 1401 is sealed with a patch 1403. A filling device, for example a syringe needle 1404 attached to a syringe 1406, can be inserted through the patch 1403 to dispose fluid 1405 in the implant 1400. After fluid has been disposed in the outer container 1401, the syringe needle 1404 can be removed, and a patch (not shown) can be disposed over the injection site to seal the outer container 1401.

Figure 17:
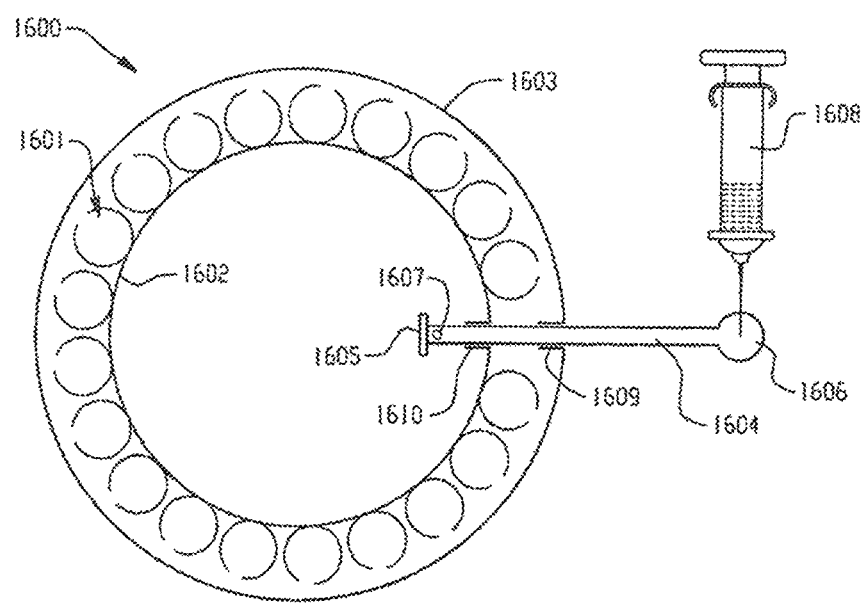
FIG. 17 shows a cross-section of a breast implant having open members attached to an inner container showing introduction of a fluid into the inner container via a filling tube.

With reference to FIG. 17, implant 1600 having open members 1601 attached to inner container 1602 disposed in outer container 1603 is evacuated (FIG. 16) and then implanted into a subject. Outer container 1603 is filled with a fluid (not shown). Filling tube 1604 extends from inside inner container 1602, through outer container 1603, and outside the body of the subject. Filling tube 1604 has detachable plug 1605 connected to the end disposed in inner container 1602 and injection port 1606 at the end of filling tube 1604 external to the subject's body. Hole 1607 near detachable plug 1605 allows fluid communication through filling tube 1604 among inner container 1602 and injection port 1606. Filling device 1608 can connect to injection port 1606 for fluid sourcing and exchange with the implant. Pilling device 1608 can be manual or automated. Filling tube 1604 traverses primary valve 1609 disposed on the outer container and secondary valve 1610 disposed on inner container 1602. Fluid is introduced into inner container 1602 to adjust implant 1600 to a desired volume, and filling tube 1604 is removed from implant 1600. Removal of filling tube 1604 can be achieved by pulling on filling tube 1604 with an amount of force effective to seat detachable plug 1605 in secondary valve 1610 and to detach plug 1605 from filling tube 1604. Filling tube 1604 is pulled from outer container 1603 through primary valve 1609. In this way, primary valve 1609 seals implant 1600, and secondary valve 1610 seals inner container 1602.

In an embodiment, the members are open members. When the outer container is filled with the fluid, the volume of the outer container increases from the compressed state. Likewise, the member (due to its opening) fills with the fluid that is introduced into the outer container. In this way, the member reverts to its pre-compressed, original shape or size or a substantially similar shape or size.

Figure 18:
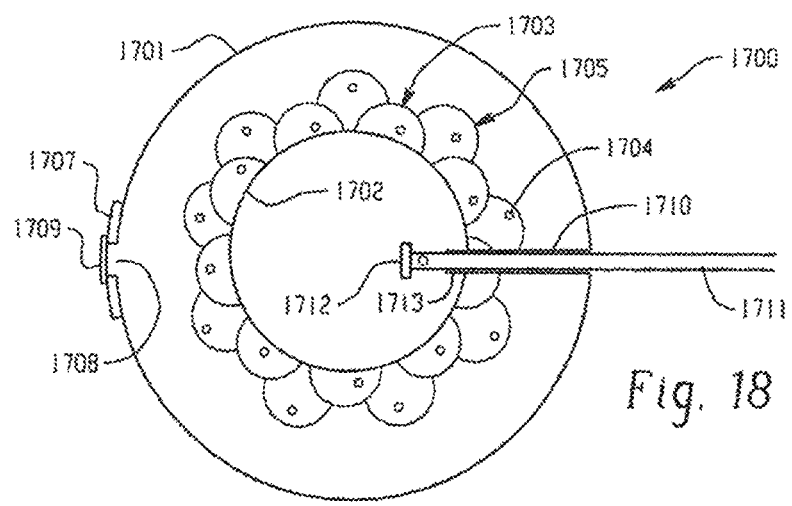
FIG. 18 shows a cross-section of a breast implant having semi-shell members attached to an inner container with a filling tube and also having a seal disposed on an injection site of an outer container.

In another embodiment, as shown in FIG. 18, implant 1700 is inserted into a subject and includes outer container 1701, inner container 1702 disposed in outer container 1701, a first layer of semi-shell members 1703 disposed on inner container 1702 and having openings 1704 for fluid transmission, and a second layer of semi-shell members 1705 disposed on the first layer of semi-shell members 1703. Inner container 1702 and members (1703, 1705) are inserted into outer container 1701 through opening 1708 that is then sealed with, for example, patch 1707. A filling tube is inserted into aperture 1708 in patch 1707, and outer container 1701 and members (1703, 1705) are filled with a fluid. Thereafter, the filling tube is removed from outer container 1701 and aperture 1708, and aperture 1708 is sealed with seal 1709 (e.g., a patch or plug). Duct 1710 interconnects outer container 1701 and inner container 1702, and filling tube 1711 traverses duct 1710. Filling tube 1711 extends from inside inner container 1702 to the outside of outer container 1701 to be disposed outside the subject's body. Filling tube 1711 includes detachable plug 1712 that is disposed in inner container 1702 to seal inner container 1702 in response to removal of filling tube 1711 from implant 1700. Thus, filling tube 1711 is removably disposed in duct 1710. Valve 1713 seals inner container 1702 in response to detachable plug 1712 being seated in valve 1713 when filling tube 1711 is removed.

Figure 19:
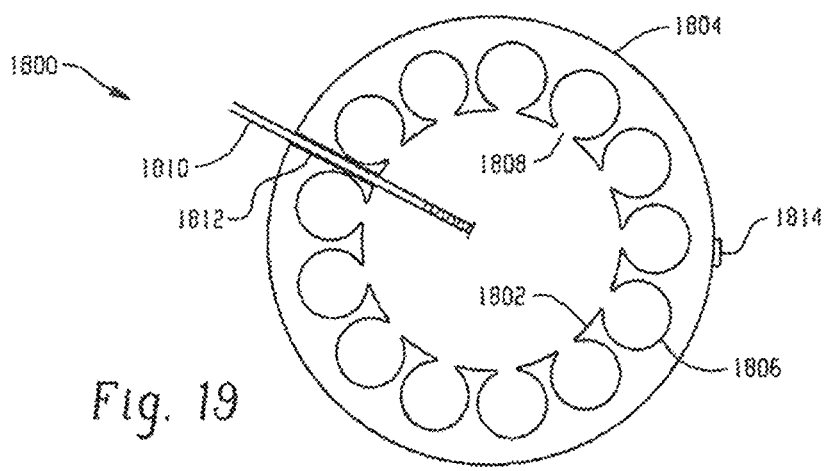
FIGS. 19 and 20 show cross-sections of an implant having members attached and in fluid communication with an inner container.
Figure 20:
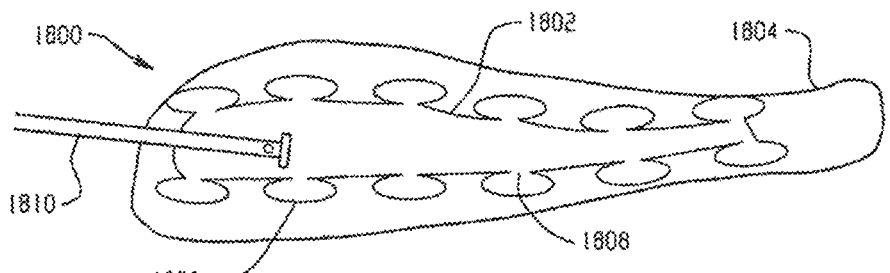

In an exemplary embodiment, as shown in FIGS. 19 and 20, implant 1800 includes inner container 1802 disposed in outer container 1804. Member 1806 is disposed and attached to inner container 1802. Inner container 1802 and member 1806 can be molded as a single item or can be made separately with members 1806 being attached to the inner container 1802 in a separate process. Fluid channels 1808 connect member 1806 to inner container 1802 so that fluid can flow therebetween. Member 1806 can have various shapes as described herein for members. Filling tube 1810 is disposed in inner container 1802 and extends through and beyond outer container 1804. Duct 1812 can optionally be disposed between inner container 1802 and outer container 1804 through which filling tube 1810 can extend to connect inner container 1802 to a fluid source (not shown). Patch 1814 is disposed on the surface of outer container 1804 to seal outer container 1804.

As shown in FIG. 20, implant 1800 can collapse in response to evacuation of its contents, including air or a liquid, for example. Members 1806, inner container 1802, and outer container 1804 are flexible so that evacuation of, for example, inner container 1802 through fill tube 1810 causes implant 1800 to collapse. Such collapse is advantageous in the insertion of implant 1800 in a patient.

Figure 21:
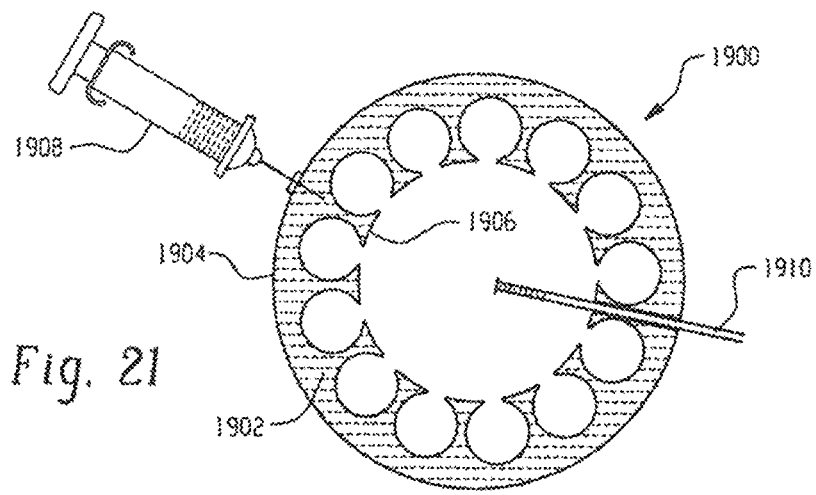
FIGS. 21, 22, and 23 show cross-sections of the implant of FIGS. 19 and 20 during various events associated with filling the implant with a fluid.
Figure 22:
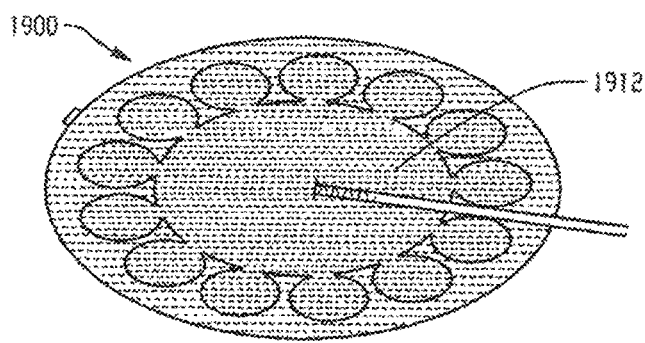
Figure 23:
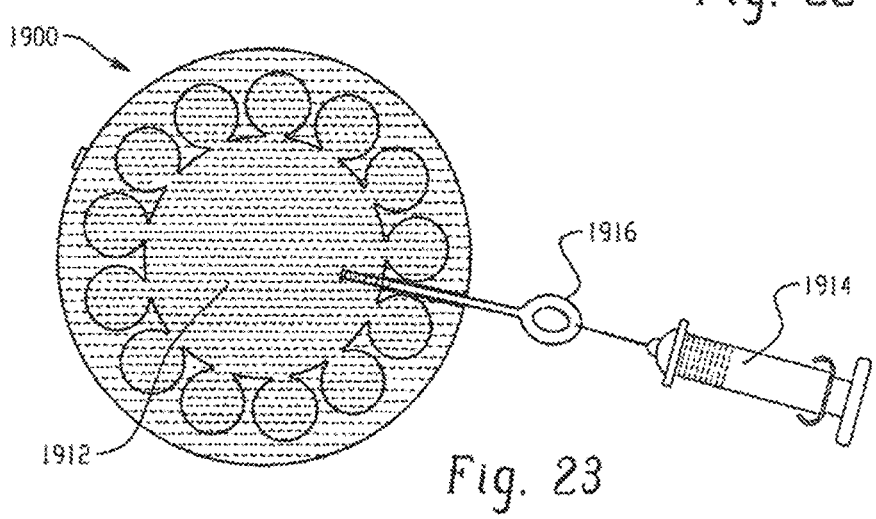

In an embodiment illustrated in FIGS. 21, 22, and 23, prior to insertion in a subject (e.g., a breast surgery patient), outer container 1904 of implant 1900 is filled (e.g., fully or partially filled) with fluid 1902 (e.g., saline) via syringe 1908 (or other implement configured to dispose a fluid in outer container (1904). Inner container 1906 has filling tube 1910 disposed therein to dispose fluid or evacuate inner container 1906. Upon insertion of implant 1900 into the subject, inner container 1906 is filled with fluid 1912 via filling tube 1910 (FIG. 19B). The amount of fluid 1912 can be less than the volumetric capacity of inner container 1906 so that in a subsequent procedure (which can occur several months or years after the initial implantation of implant 1900) implant 1900 can be expanded to a larger volume by addition of additional fluid 1912 injected via syringe 1914 into port 1916 of filling tube 1910. Similarly, the volume of implant 1900 can be reduced by extraction of some of fluid 1912 in inner container 1906 via filling tube 1910. After final adjustment of the size of the implant, filling tube 1910 can be removed from implant 1900.

According to another embodiment, an implant is inserted into a subject and has a primary tube removably disposed in the outer container to transmit fluid to or from the outer container. Members are disposed in the outer container, and the implant also has a primary valve disposed on the outer container to seal the outer container in response to removal of the primary tube. A secondary tube is removably disposed in the outer container and the inner container to transmit fluid among the inner container and the same or another fluid source disposed external to the outer container. A secondary valve is disposed on the outer container to seal the outer container in response to removal of the secondary tube, and a tertiary valve is disposed on the inner container to seal the inner container in response to removal of the secondary tube. Using the primary and secondary tubes, the volume of the outer container, members, and inner containers can be adjusted with addition or removal of a fluid to a desired volume.

As shown in FIGS. 24 and 25, a breast implant can have self-sealing valve 58 that includes sealing aperture 54 and tube 52 through which filling tube 60 can be inserted (instead of, e.g., injection site patch 1814 as in FIG. 19). Self-sealing valve 58 can be part of an outer container patch or can be part of outer container 50 of the implant.

Beyond self-sealing valve 58, other valves can be used with the implant. Examples of such valves include a check valve, duckbill valve, diaphragm valve with an external or internal plug, reed valve, leaf valve, cross slit valve, or the like. The valve prevents the fluid from exiting the implant. The valve can be integrally formed with an outer or inner container during a manufacturing process.

The outer container provides a shield against loss of the fluid into a patient after implantation of the implant. Further, if fluid leaks from the outer container, the loss of volume of fluid would be finitely inconsequential. Without being bound by theory, for an embodiment in which the fluid contains a small amount of silicone gel, none or substantially none of the silicone gel would leak from the implant herein since the silicone gel attaches to the internal surface of the outer container and the external surface of the members or an inner container.

The fluid used to fill the inner container, outer container, or member is noncorrosive and is compatible with the materials of construction herein as well a biological tissue or biological fluids. The fluid can have different hydrophobic or hydrophilic properties from those of the inner container, outer container, and member. The volume of the fluid inside the outer container of the implant is about 1% to about 120%, specifically about 5% to about 80%, more specifically about 5% to about 30% of the nascent volume of the outer container. Moreover, the volume of the fluid contained within the outer container enhances mobility of the members and inner container disposed in the outer container while dampening motional disturbances of the fluid due to, e.g., a movement or impact of the outer container when implanted into a subject. The volume of the fluid in the outer container is about 5 cc to about 500 cc, specifically about 5 cc to about 200 cc, and more specifically about 5 cc to about 150 cc. In an embodiment, the volume of the fluid is determined based on the volume of the outer container, volume of the members and inner container, and consideration of aesthetic parameters. The volume of the fluid introduced into the implant is selected by such factors as reduction of rippling of the breast implant or optimization of the shape of the breast implant as well as volume adjustment to correct asymmetry so that both breasts after implantation appear to be of the same size, either during insertion or post-operatively such as by a detachable injection port attached at an end of a filing tube that is external to the subject's body.

By selection of the ratio of the volume of the members and the inner container to that of the fluid in the outer container, the effective viscosity of total medium (the member, inner container, and fluid) can be controlled and varied to form a breast implant that exhibits a highly realistic, aesthetically pleasing appearance. The volumetric amount of the members and the inner container in the fluid is about 10 vol % to about 95 vol %, specifically about 20 vol % to about 90 vol %, and more specifically about 40 vol % to about 80 vol %, based on the total volume of the members, inner container, and fluid.

The fluid is biocompatible and can be bio-absorbable. The fluid used in the outer container, inner container, and member can be the same or different. Exemplary fluids include saline, silicone, polyvinyl pyrrolidone, hyaluronic acid, polyacrylamides, polysaccharides, dextran, hydrogel (e.g., methylcellulose hydrogel), povidone, triglycerides, cellulose, derivatives of the foregoing, or a combination comprising at least one of the foregoing.

In certain embodiments, implant 2000, as in FIG. 26, can have various members disposed in outer container 2002. The implant optionally can include inner container 2018. Exemplary members include member 2004 with no opening (e.g., a testicular implant pre-filled with a fluid or a solid, elastomeric member); member 2006 having opening 2008 disposed on its surface for fluid communication with outer container 2002; semi-shell member (2010, 2012, 2014, wherein some of the semi-shell members open towards each other as in 2010; some of the open shell members abut one another as in semi-shell members 2012; some of the open shell members point in a same direction as in semi-shell members 2014); member 2016 in fluid communication with inner container 2018, and the like. Combination of members (2004, 2006, 2008, 2010, 2012, 2014, 2016) can be used together. Additionally, valve 2020 can be disposed on inner container 2018 and outer container 2002 to admit fluid and to seal each container.

With reference to FIG. 27, in an additional embodiment, implant 2000 includes projections 2022. Projections 2022 can be finger-like in that they are radially disposed on the surface of inner container 2018. Projections 2022 can have a length of about 2 mm to about 25 mm, and specifically about 2 mm to about 20 mm. The transverse cross-sectional shape of projections 2022 can be any shape including circular, polygonal, oval, star, and the like. The largest linear dimension in the transverse cross-section can be about 2 mm to about 15 mm, and specifically about 2 mm to about 10 mm. Furthermore, projections 2022 can have a hollow space (continuous with the interior of inner container 2018), can be solid without such a space, or a combination thereof. Projections 2022 and inner container 2018 can be molded in a single piece or can be made separately with projections 2022 being later attached to inner container 2018. Alternatively, during manufacture of inner container, projections 2022 can be made by placing inner container 2018 in a mold having a plurality of through holes disposed in the mold surface and pressurizing inner container 2018 with a gas in order to expand portions of inner container 2018 through the holes in the mold, producing projections 2022. In an embodiment, projections 2022 can be softer and more elastic than inner container 2018 so that the projections have a floppy effect in a fluid inside outer container 2002. In one embodiment, an exterior surface (e.g., a tip) of projection 2022 is attached to the interior surface of outer container 2002.

Figure 28:
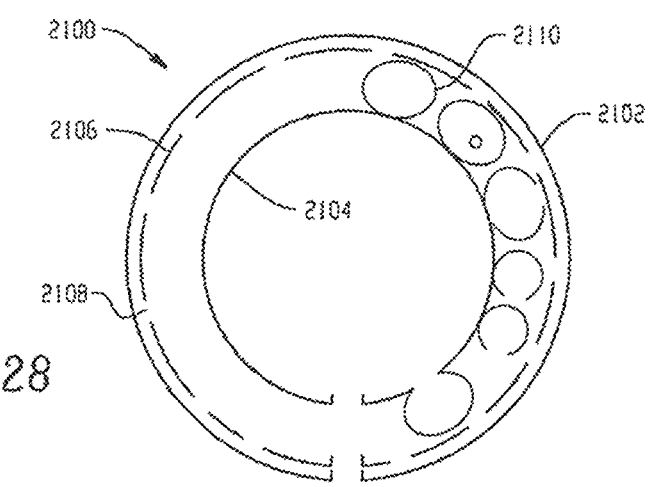
FIG. 28 shows a cross-section of an implant having a plurality of nested containers and members.

Referring to FIG. 28, according to yet another embodiment, implant 2100 includes nested containers such as outer container 2102, inner container 2104, and intermediate container 2106. Although three nested containers (2102, 2104, and 2106) are indicated, the number of nested containers is not limited thereto. Furthermore, inner container 2104 or intermediate container 2106 can have opening 2108 (an aperture, perforation, slit, and the like) disposed therethrough to allow fluid communication between the container (2106 as shown in FIG. 21) and a surrounding container (2102 as show in FIG. 21). In an embodiment, member 2110 can be disposed between any two containers (2102, 2104, and 2106) or the interior of inner container 2104.

Figure 29:
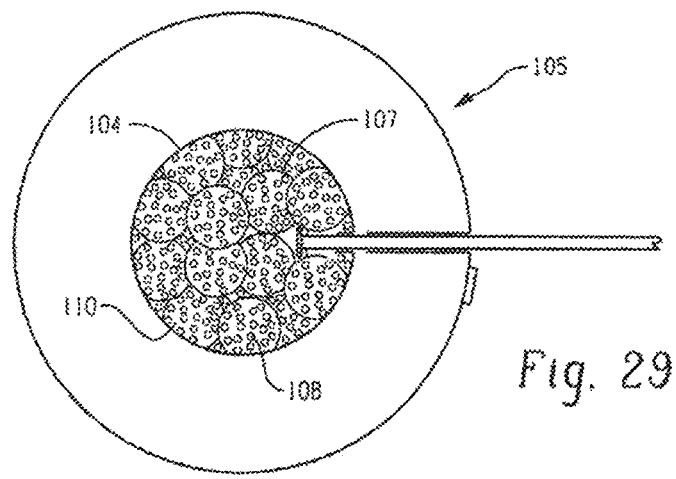
FIG. 29 shows a cross-section of an implant showing optional containers disposed in an inner container.

As previously mentioned, the implant can have members disposed in an inner container. FIG. 29 shows breast implant 105 with inner container 104 that contains member 107. Members 107 can have pores 108 for flow of fluid 110 inside inner container 104. Alternatively, the member can be closed without permitting communication of fluid between the interior and exterior of member 108. Such closed members can contain fluid or can be solid.

Figure 30:
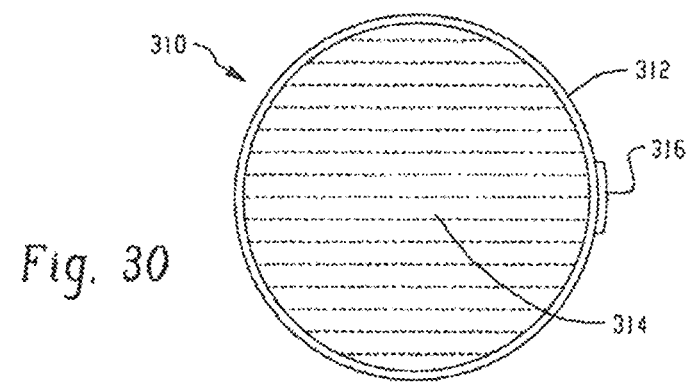
FIG. 30 shows a cross-section of a member having an injection patched attached thereto.

Also as previously indicated, a member can be made of various materials and have various shapes. As shown in FIG. 30, member 310 (e.g., a testicular implant) has shell 312 (e.g., a shell with a hollow internal space) and contains sub-fluid 314. Subfluid 314 is introduced into member 310 through a perforation in shell 312. Patch 316 seals the perforation on the surface of shell 312. According to an embodiment, sub-fluid 314 is introduced into member 310 by inserting a filling tube or syringe needle into shell 312, creating a perforation, or shell 312 is made with an opening or a valve for sub-fluid introduction. Patch 316 adheres to the surface of shell 312 with an adhesive such as a silicone-based glue or other biocompatible sealant as above. Patch 316 can be the same or different material as shell 312 of member 310. Moreover, the pressure inside member 310 can vary depending on the amount of sub-fluid 314 introduced. As a result, the flexibility and compressibility of member 310 is variable.

In another embodiment, the member is a solid body without a hollow internal space.

The number of members inside a container of the implant herein can vary from one up to as many members as the volume of a container can hold without rupturing or adversely affecting the structural integrity of the container (e.g., an inner, intermediate, or outer container). Since the container herein is flexible and expandable, the volume of the members inside the container can be about 1% to about 120%, specifically about 25% to about 110%, more specifically about 50% to about 90% of the volume of the container before any expansion of the container beyond it nascent volume.

The shape of the members can vary. In an embodiment, the cross-sectional shape of the members is circular, ellipsoidal, crescent, irregular, or a combination thereof. The shell of the member is flexible so that its shape under compression can change to accommodate forces exerted on the container of a breast implant. Alternatively, the shell is rigid so that the members provide further structural integrity and support to the shape of the breast implant.

Figure 31:
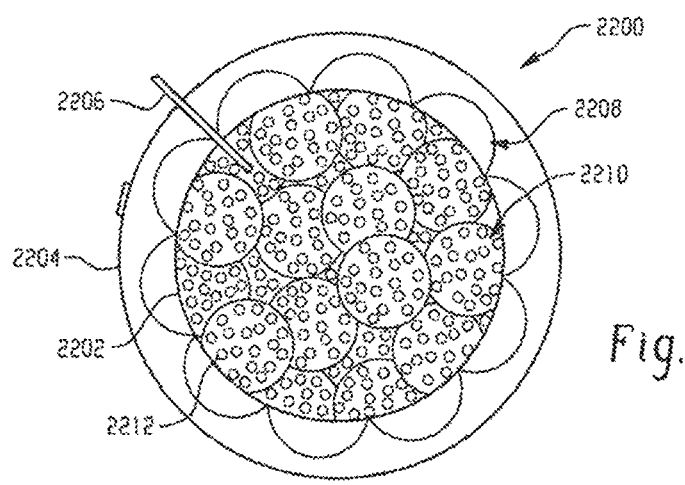
FIG. 31 shows a cross-section of an implant having members disposed in an inner container and interposed between the inner container and an outer container.

In some embodiments, the inner and outer containers of an implant independently can contain members. In a non-limiting embodiment, as shown in FIG. 31, implant 2200 includes inner container 2202 disposed in outer container 2204, filling tube 2206 traversing outer container 2204 and disposed in inner container 2202, members 2208 interposed between outer container 2204 and inner container 2202, and members 2210 having openings 2212 disposed in inner container 2202. It is contemplated that any type of member described herein can be used in either of inner 2202 or outer 2204 containers.

Figure 32:
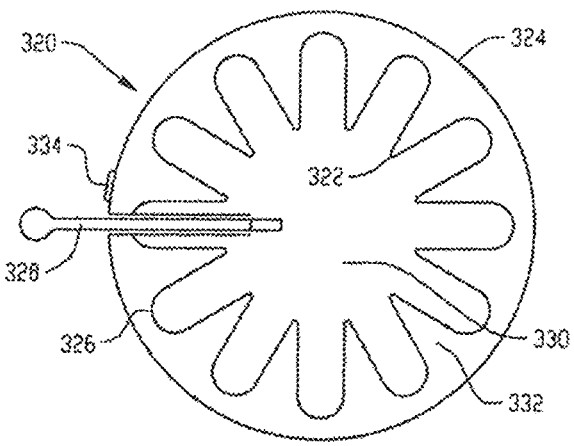
FIGS. 32 and 33 are cross-sections of implants with an inner container having projections.
Figure 33:
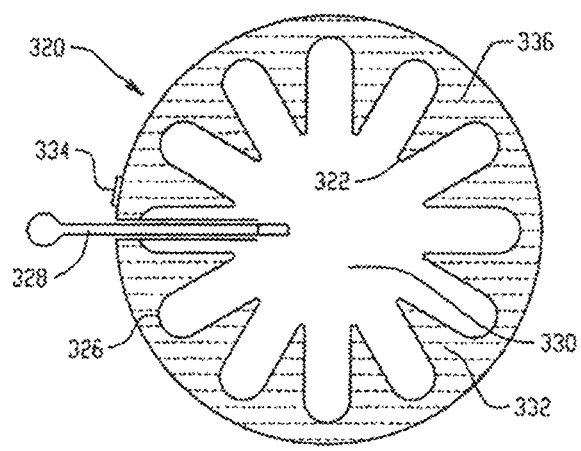

FIG. 32 shows breast implant 320 with inner container 322 and outer container 324. Inner container 322 has projections 326 protruding from a surface thereof. Projections 326 can be made separately from (and subsequently attached to) inner container 322, or inner container 322 can be made integrally with projections 326 as a single item. Breast implant 320 also has filling tube 328 to fill space 330 of inner container 322. Inner 322 and outer 324 containers can have a different pressure from each other such that a pressure differential exists at the surface of inner container 322 that separates space 330 from interstitial space 332 between inner container 322 and outer container 324. Patch 334 is disposed on an external surface of outer container 324 to cover and seal a perforation, which allows transfer of fluid or members into outer container 324. Breast implant 320 can contain a fluid, and different fluids can be disposed in inner 322 and outer 324 containers. As depicted in FIG. 33, breast implant 320 can have interstitial space 332 filled with, e.g., gel 336 while space 330 is filled with a different fluid, e.g., saline. The different fluids in space 330 and interstitial space 332 can contribute to a more natural feel and also contribute to moderation of fluid motion in breast implant 320. Again, the pressure and volume can differ between inner 322 and outer 324 containers to satisfy a patient's needs.

Figure 34:
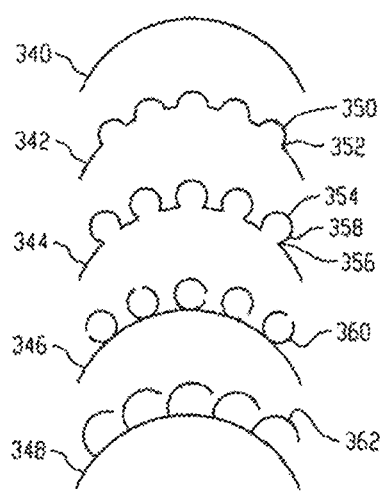
FIG. 34 shows variations of a surface of an inner container.
Figure 35:
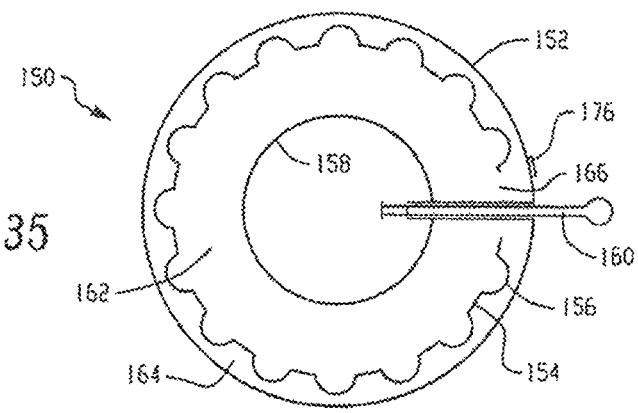
FIGS. 35 through 39 show cross-sections of an implant with an outer container surroundingly disposed about nested inner containers arranged such that an inner container includes projections.
Figure 36:
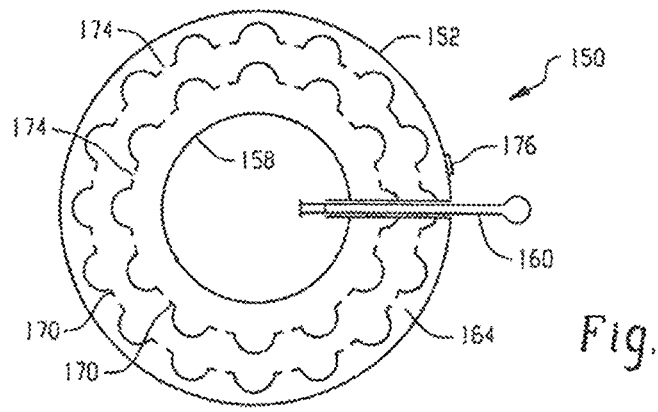

As previously described, the surface of an inner container can have various surface contours (e.g., projections) or members attached thereto. FIG. 34 shows possible variations of a surface of a container. A surface of container 340 can be substantially smooth over a portion of the surface or be smooth in a portion with a distribution of projections or members over some portion of the surface. The surface of container 342 can have projections 350 that have base 352 that is the largest size of the projection. Container 344 can have projections 354 that have base 356 that is smaller than larger portion 358 of the projection 354. Members 360 (open or closed) can be attached to container 346. Additionally, semi-shell members 362 can be attached to container 348. These surfaces can have an opening to communicate fluid therethrough or can be a continuous surface without an opening. Any combination of the foregoing surface features can be used.

The implant can have nested inner containers as, e.g., in FIGS. 35 through 40, 42, and 43. In a particular embodiment shown in FIG. 35, implant 150 has outer container 152, inner container 154 (also referred to as an intermediate container) with projections 156, and inner container 158 that is substantially smooth. Intermediate container 154 is interposed between outer container 152 and inner container 158. Further, inner container 158 is equipped with filling tube 160 for disposal of fluid therein independent of fluid volume in spaces 162, 164. Fluid can flow between intermediate container 154 and outer container 152 through opening 166 in intermediate container 154. In an embodiment, implant 150 can have several intermediate containers 170 that have openings 174 distributed on intermediate containers 170, 172. Patch 176 attached to outer container 152 can seal an opening therein that is used for provision of a fluid into outer container 152.

Figure 37:
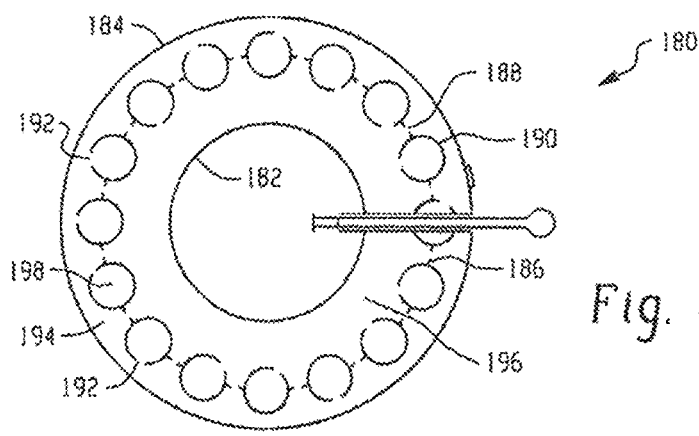
Figure 38:
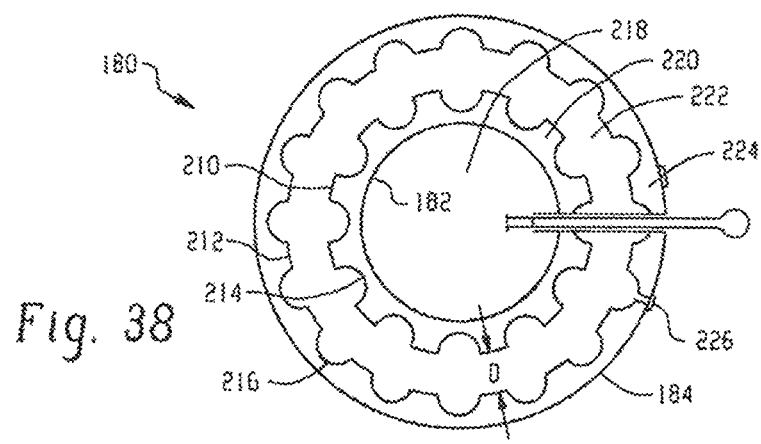
Figure 39:
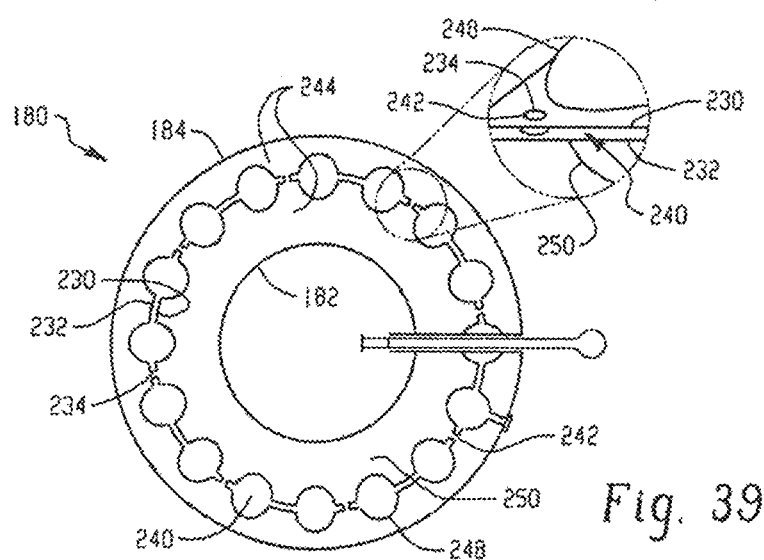

In an embodiment as shown in FIG. 37, implant 180 has intermediate container 186 interposed between inner container 182 and outer container 184. Intermediate container 186 has openings 188 and members 190, which are disposed in intermediate container 186. Member 190 can have opening 192. Opening 192 in member 190 can open to space 194 external to intermediate container 186 or to space 196 internal to intermediate container 186. Thus, fluid can communicate into member 190. For a member that has openings 192 that connect internal space 198 of member 192 to spaces 194 and 196, fluid can communicate between space 194 and 196 via internal space 198 of member 190. As a result, fluid flow in implant 180 is baffled to a great extent such that implant 180 achieves a more realistic feel and appearance of natural biological tissue when implanted into a subject. As in the embodiment shown in FIG. 38, implant 180 is similar to that shown in FIG. 37. Here, two intermediate containers 210, 212 are interposed between inner 182 and outer 184 containers. Intermediate containers 210, 212 have projections 214, 216 that project from one another in opposing radial directions. In addition, intermediate containers 210, 212 are displaced from one another by distance D. It is contemplated that distance D can be any value, e.g., from 0.1 mm to 50 mm, without limitation. Spaces 218, 220, 222, 224 can be independently filled to attain distinct volumes of fluid. In an embodiment, space 222 can be filled via an opening (not shown) that is subsequently sealed with patch 226. Thus, spaces 218 through 224 can be different volumes of fluid, different fluids, and attain different pressures as selected. FIG. 39 (and its corresponding inset) indicates that intermediate containers 230, 232 can be attached to one another at connector 234. Connector 234 can be of the same material as inner 182 or outer 184 container or can be a different material. Further, connector 234 can be springy or rigid such that intermediate containers 230, 232 are maintained from each other at some distance, which can, but does not have to, vary along the circumferential direction of intermediate container 230. Connector 234 can be a partition between space 240 (among intermediate containers 230, 232) and opening 242. Opening 242 communicates and buffers fluid flow between spaces 244 that occur between containers 182, 184, 230, 232. Further, projections 248, 250 can be disposed on the surfaces of intermediate containers 230, 232. It should be noted that opening 242 baffles while maintaining fluid flow radially among spaces 244 while projections 248, 250 can baffle non-radial, angular flow of fluid within spaces 244 such that abrupt motion or "sloshing" of the fluid in the implant 180 is decreased.

Figure 40:
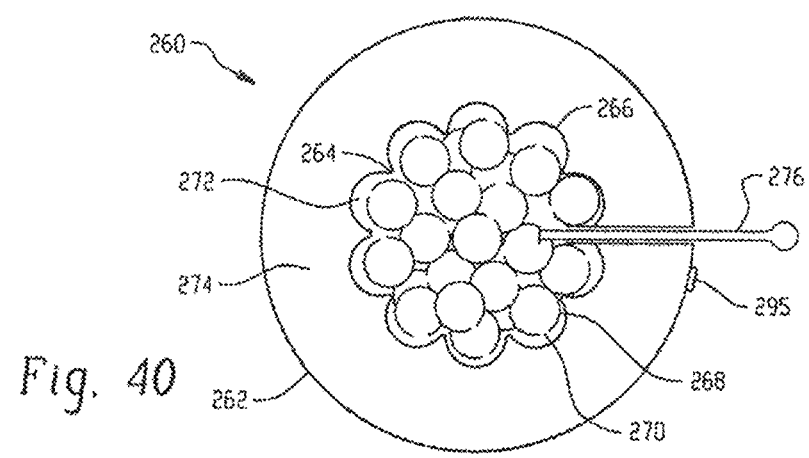
FIG. 40 shows a cross-section of an implant with members disposed in an inner container and surrounded by a fluid inside an outer container.

As shown in FIG. 40, implant 260 includes outer container 262 and inner container 264, which may be free-floating or not. Inner container 264 includes a plurality of projections 266 that project from a surface thereof. Projections 266 can be formed as a structural feature of inner container 264 such that a nascent shape of the inner container has projections 266. Alternatively, projections 266 can be a result of force applied on inner container 264 by a fluid in inner container 264 or by conforming around members 268 disposed in inner container 264. Member 268 can be closed or open. An open member can have opening 270 to communicate fluid between internal space 272 of member 268 and inner container 264. Members 268 can be attached to one another or to the inner surface of inner container 264. Implant 260 can contain different fluids disposed in outer container 262, inner container 264, and members 268 (in the case of closed members). In an embodiment, space 274 between outer container 262 and inner container 264 can be filled with, but not limited to, a gel, while inner container 264 and members 268 can be filled with, e.g., saline. Filling tube 276 traverses outer container 262 and terminates in inner container 264 for filling or removing fluid in the inner container 264 or members 268. Patch 295 is affixed to the outer container 262 as a seal in some embodiments.

Figure 41:
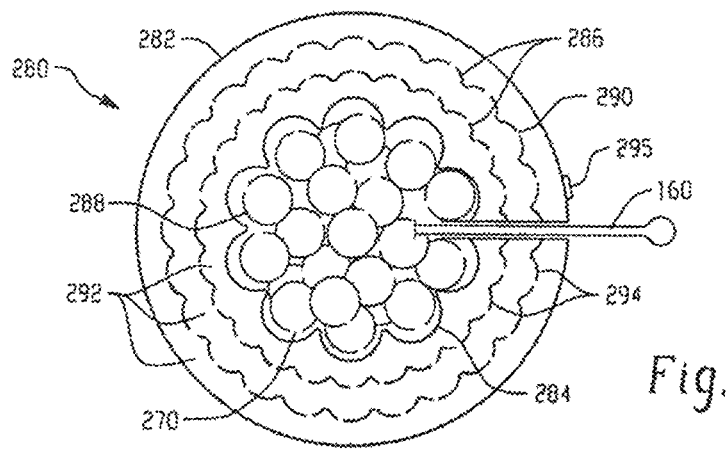
FIG. 41 shows a cross-section of an implant having nested inner containers with openings and projections and that are disposed in an outer container and having valves independently attached to that to the inner and outer containers.
Figure 42:
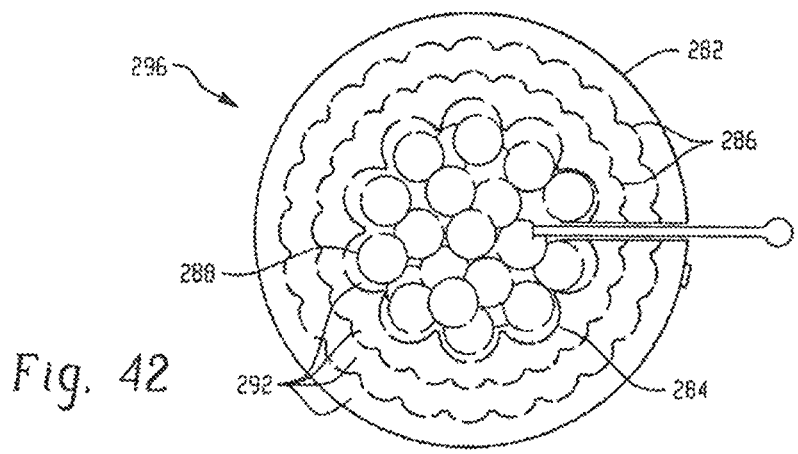
FIG. 42 shows a cross-section of an implant having nested inner containers having a single valve attached thereto and also openings and projections that are disposed in an outer container such that all chambers are in fluid communication with each other.

With reference to FIG. 41, implant 280 includes outer container 282, free-floating inner container 284, nested intermediate containers 286. Inner container 284 can be free-floating and contain members 288 disposed therein as well as projections 294 on its surface. A combination of closed or open members 288 can be attached to one another or to the inner surface of inner container 284, or members 288 can be free-floating. Openings 290 in 286 intermediate containers or inner container 284 communicate a fluid between spaces 292. Nested intermediated containers 286 can be concentric or may be disposed asymmetrically with respect to one another or inner 284 or outer container 282. FIG. 42 shows implant 296, similar to implant 280 in FIG. 41. Implant 296 includes inner container 284 having opening 298 therein for fluid communication among members 288, and spaces 292.

The implant herein closely approximates natural, healthy breast tissue, particularly with respect to the hydrodynamic properties of the implant filled with a fluid. According to Pascal's law a change in pressure applied to an enclosed fluid is transmitted undiminished to every point of the fluid and the walls of a containing vessel. R. A. Serway, *Physics*, 413 (Saunders 1990). To decrease the transmission of the pressure change through the fluid to the walls of the implant, a member can be disposed along the fluid communication path in the implant to obstruct the transmission of the motion and absorb energy from the travelling wave. Thus, the amplitude of the disturbance at a wall of the implant diminishes through the implant due to the baffling effect of the members. Moreover, for the implants herein with an elastic wall (e.g., the outer or inner container, which can flex, bend, or otherwise deform under a pressure change), the amount of disturbance at the elastic wall and corresponding displacement of the elastic wall decreases due to inclusion of such a baffling member in the fluid communication pathway. Consequently, the implant herein occasions an effective fluid viscosity that well-approximates that of natural, healthy breast tissue. In addition, the inclusion of for example, the semi-shell members attached to an inner container advantageously affect the fluid motion of the breast implant and aesthetic presentation of the implant.

Moreover, the implants use biologically safe materials. Such materials have gained approval from the United States Food and Drug Administration (FDA), and the implant constructed of these materials has a feel that emulates that of biological tissue. Surface rippling is diminished or eliminated in the implants herein. Further, the disclosed implant can be efficiently manufactured and at a low relative cost.

Since FDA approved materials can be used in the construction of the implants herein, the need or length for further regulatory approval studies may be greatly reduced. In addition to the saline-filled members and inner container, no additional filling material is introduced for the breast implant although the embodiments are not limited thereto. Saline as well as other lubricants can be added between the outer container and the members and inner container. Consequently, the disclosed breast implant has enhanced safety factors. Moreover, a filler such as a coil, tube, or rod of elastic polymer material (e.g., polystyrene, silicone, polyurethane, polyimide, and the like) also can be disposed with the members or inner container in the outer container for further baffling or shaping purposes of the implant.

Breast implants of conventional filling materials (saline and silicone gel) can have a limited lifetime. An end of life of such implants can result from rupture of the outer shell of the implant. Rupture of a saline implant can result in nearly total deflation of the implant, i.e., near complete loss of the saline. Rupture of the silicone gel implant can result in migration of the silicone gel out of the shell, which can result in encasement of the silicone gel by the subject's body, e.g., so-called capsular contracture of the silicone gel. Rupture of an implant can require another surgery to replace the implant or evacuate the leaked filling material, e.g., silicone gel. Moreover, saline-filled implants can have an unnatural feel. The hydrostatic properties of the saline fluid can distort the outer shell as the tissue surrounding the implant moves the implant. Such disturbance of the implant can increase the leak rate of the implant. As noted above, an embodiment of the breast implant disclosed herein does not suffer from these problems. In an instance where the fluid in the outer container is, e.g., silicone gel, the members can diffuse the fluid evenly (e.g., see FIGS. 19 and 23). Also, less gel is used to fill the outer container. If the outer container ruptures, such gel adheres to the members disposed in the outer container. Consequently, there is less likelihood of gel leaking out of the outer container.

The tactile feel of the breast implant herein is superior to a conventional breast implant since the breast implant herein is filled with members in a fluid that provide a consistency more closely approximating normal breast tissue. Thus, the breast implants herein move with a motion similar to breast tissue. Additionally, the fluid lubricates the members that support the outer container. As a consequence, the breast implant has a low probability of fold flaw failure and rupture due to rippling.

In another embodiment, the implant is a tissue expander. In contrast to breast reconstruction where a tissue expander is performed by placing a tissue expander beneath muscle, the tissue expander herein is disposed beneath or above muscle. In a particular embodiment, the tissue expander is disposed above muscle. As used herein, "above the muscle" refers to a location between muscle and skin; "below muscle" refers to an anatomical location between muscle and bone tissue.

The tissue expander is an integral expander and has an injection port attached to an anterior surface of the tissue expander. In this manner, the tissue expander is configured to be expanded post-operatively. According to an embodiment, expansion of the tissue expander post-operatively is accomplished by inserting a needle into the port and injecting saline to stretch the muscle and overlying skin.

In an embodiment, a patient is subjected to a skin sparing mastectomy whereby expansion breast reconstruction is performed by placing the tissue expander above the muscle in the patient. It is contemplated that some integral valve tissue expanders placed beneath the muscle are not suitable for above-muscle disposal because such an expander is, e.g., too bulky or irregular in shape. When the tissue expander herein is placed above muscle, it is disposed without any fluid in some embodiments so that there is no tension on the overlying skin. In an embodiment, the tissue expander has an injection port attached by means of a fill tube and located remotely from the tissue expander at the reconstruction site. To expand the tissue expander, the remote injection port (which is placed at a distance from the breast under the skin) is filled postoperatively by injecting saline into the port. An advantage of the tissue expander is that it is fully supported so that it does not collapse when placed in the patient or during filling. Furthermore, the tissue expander is soft and flexible to provide a non-rigid, normal feel of the tissue expander without any rigid edges and without restricted expansion, no rippling when over-expanded and an absence of scalloping on the edges.

In an embodiment, the tissue expander includes a smooth, silicone outer container that houses an inner container with projections thereon. The inner container has openings on its surface, is free-floating and, due to its geometrical configuration, expands after compression to its non-compressed geometry. Further, the tissue expander retains its open, non-collapsed shape due to its elasticity. On removing air from the tissue expander, both the outer container and inner container collapse to experience a reduction in volumetric size. In some embodiments, the tissue expander is disposed in the patient without any fluid in the inner or outer container (i.e., completely empty) with the inner container supporting the tissue expander from collapse, folding, and the like. The inner container also prevents collapse or folding when completely filled or partially filled. When completely filled, the inner container is a baffle that impedes sloshing or high amplitude motion of the fluid inside the inner container or outer container. In this manner, the inner container provides fluid baffling such that a fluid, e.g., saline, has a more gel-like feel compared to a normal saline tissue expander or implant.

In an embodiment, the internal container is constructed such that the spaces between the projections are thicker than the projections. The projections are soft and flexible so as to obtain a desired feel of natural tissue, while a more rigid frame offers rigidity, allowing the inner container to self-expand.

Figure 43:
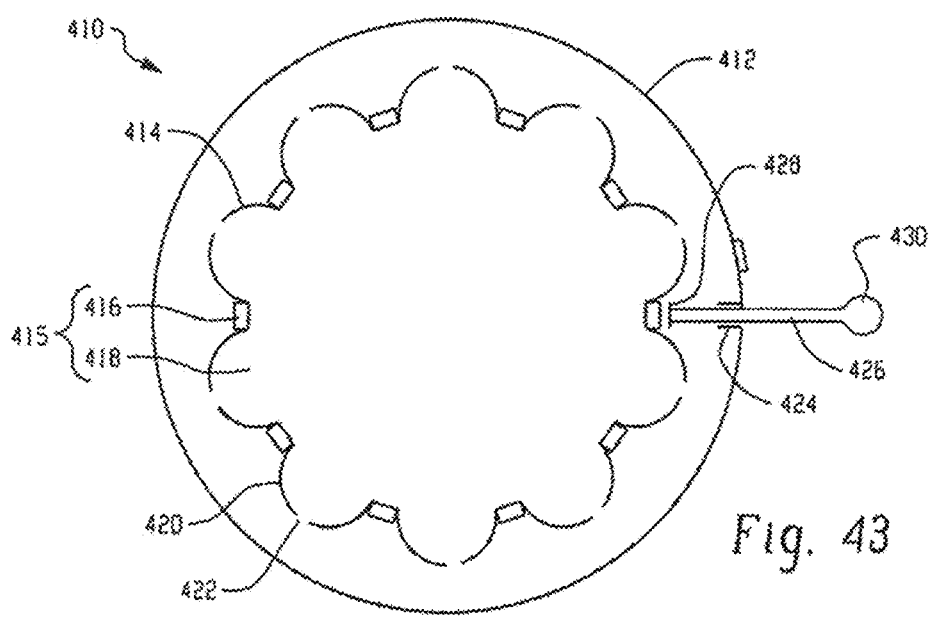
FIG. 43 shows a cross-section of a tissue expander.

As shown in FIG. 43, tissue expander 410 includes outer container 412 in which inner container 414 is disposed. Inner container 414 has reticulated frame 415. Reticulated frame 415 includes a plurality of struts 416 which interconnect, and in some embodiments form a continuous network. Struts 416 surround void 418 such that void 418 is surrounded by struts 416 in reticulated frame 415. Projection 420 connected to struts 416 covers void 418. Projection 420 is directly connected to struts 416 to form a unitary item. Projection 420 includes opening 422 by which an interior of inner container 414 is in fluid communication with outer container 412. Valve 424 is disposed through outer container 414. Valve 424 is any of the valves previously discussed and provides a path by which filling tube 426 is disposed in outer container 412 and traverses a portion of the interior space of outer container 412 to an exterior of outer container 414. Detachable plug 428 is attached to the terminus of filling tube 426, and filling tube 426 is hollow to transmit a fluid from filling port 430 into outer container 414.

Figure 44:
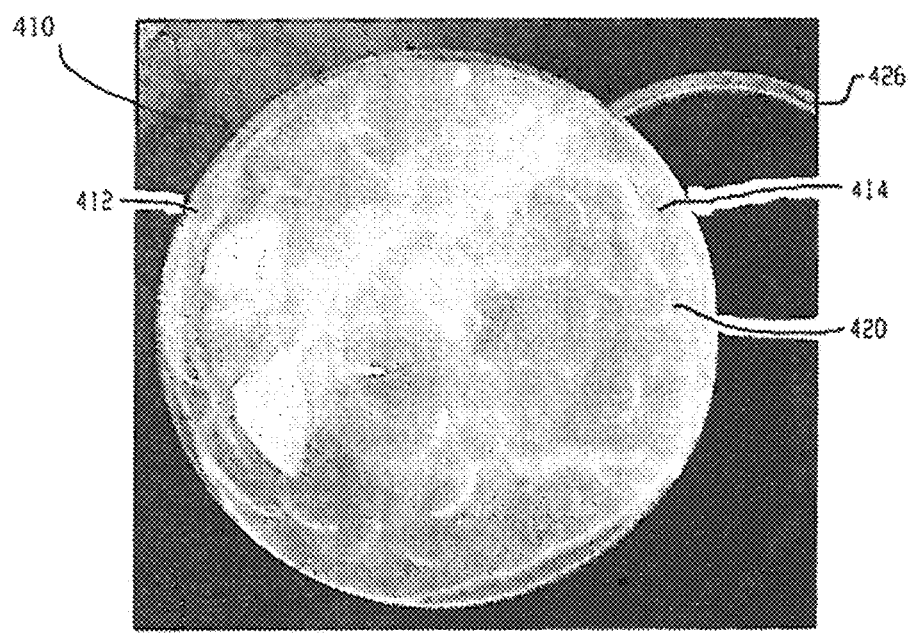
FIG. 44 shows a photograph of a tissue expander.

A photograph of the tissue expander is shown in FIG. 44. Here, tissue expander 410 is completely filled with saline via filling tube 426 such that inner container 414 and projections 420 are clearly visible through the outer container 412.

Figure 45:
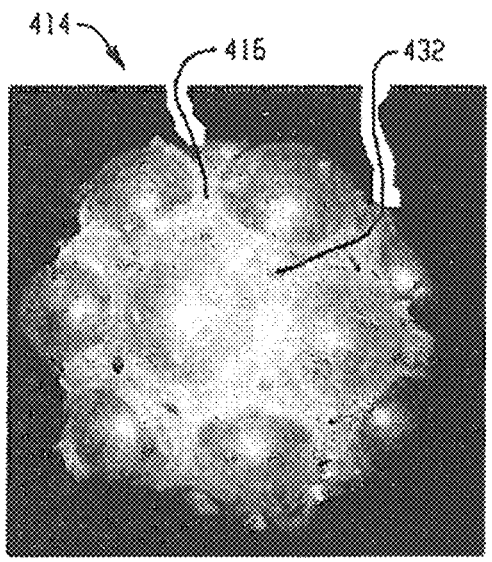
FIG. 45 shows a photograph of an inner container.
Figure 46:
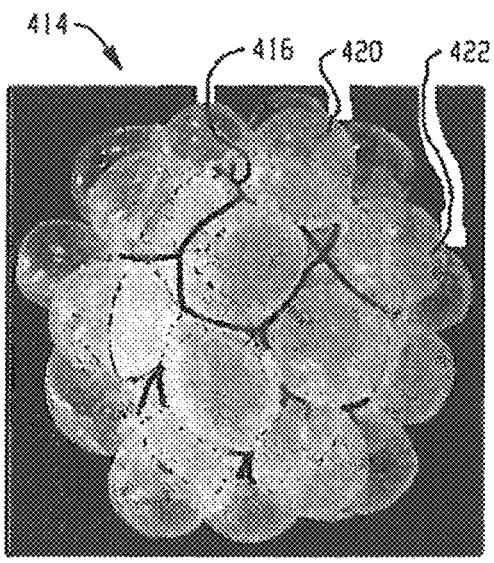
FIG. 46 shows a photograph of an inner container and curves that indicate a reticulated frame.

With regard to the inner container, the inner container provides structural support to keep the tissue expander from collapsing. As shown in FIGS. 45 and 46, photographs of inner container 414 display a plurality of projections 420 connected directly to struts 416 that connect to form the reticulated frame. In some embodiments, openings 432 are present among struts 416 as shown in FIG. 45. Openings 432 in projections 420 are indicated by grey dots in FIG. 46.

Figure 47:
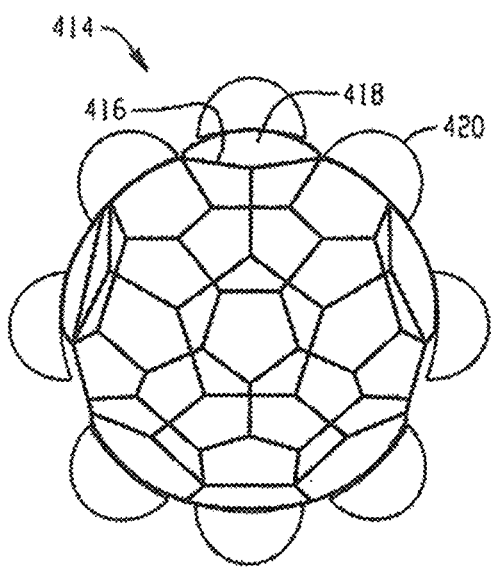
FIG. 47 shows a line drawing of a perspective view of a reticulated frame of an inner container.
Figure 48:
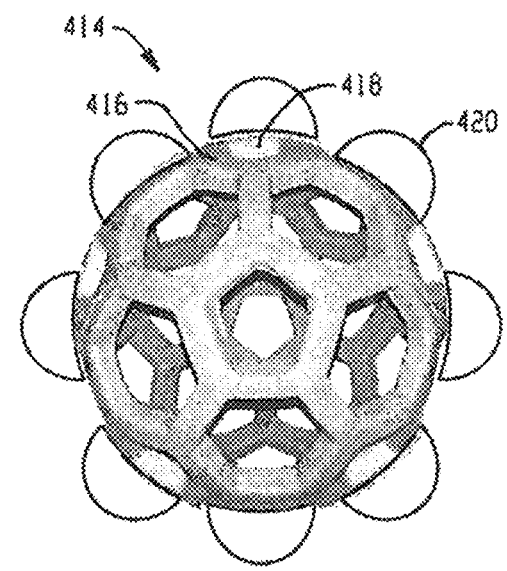
FIG. 48 shows a solid model a perspective view of a reticulated frame of an inner container.

Inner container 414 is further illustrated by the line drawing and solid model respectively shown in FIG. 47 and FIG. 48. The plurality of voids 418 is clearly depicted, and it should be observed that projections 420 are coincident with voids 418.

According to an embodiment, the inner container includes an elastomeric polymer formed in a reticulated frame structure of unitary construction. The arrangement of struts of the reticulated frame approximate vertices and edges of a polyhedron, and more particularly a truncated icosahedron, reminiscent of the chemical structure of the carbon molecule known as Buckminsterfullerene. In some embodiments, the voids and struts in the reticulated frame include regular polygons such as hexagons and pentagons as shown in FIGS. 47 and 48. In an embodiment, the voids are arranged in a repeating pattern. In an embodiment, the void has a shape such as polygonal, round, square, rectangular, triangular, ellipsoidal, or irregular. In a particular embodiment, the struts and the void of the reticulated frame are arranged in a closed polyhedral pattern. It is contemplated that the struts are arranged on a surface of the inner container, and an interior of the inner container is a hollow cavity, which is fillable by a fluid that is communicated by an opening in the projection attached to the strut. In this manner, the interior of the inner container is in fluid communication with an interior of the outer container.

It should be noted that the inner container is flexible and is configured to flex in response to a compressive force or a stretching force. The inner container then returns to an original shape in response to removal of the compressive force or the stretching force such that the inner and outer containers retain a primary shape.

The reticulated frame in the form of a Buckminsterfullerene is a polyhedron useful for the arrangement of struts of the reticulated frame of the inner container. Other polyhedral surfaces, the vertices of which can be inscribed on, e.g., a spherical or ellipsoidal surface supply the vertices and edges of the reticulated frame of the inner container.

Without wishing to be bound by theory, a polyhedral surface is a surface bounding a three-dimensional object where the surface is bounded by polygons, each edge of the polyhedral surface being shared by, e.g., two polygons. However, a polyhedron such as a tetrahedron bounded by four equal equilateral triangles, a hexahedron or cube bounded by six squares, or an octahedron bounded by eight equilateral triangles are included in a geometrical configuration of the struts of the reticulated frame herein. However, such lower polyhedral have a relatively nonspherical shape characterized by a distance between their respective faces and the spherical surface on which the vertices of those faces can be inscribed. The dodecahedron, having twelve regular pentagons as faces, and the icosahedron, having twenty triangular faces, are exemplary polyhedral surfaces for the vertices and edges of the reticulated frame. A polyhedron with more than twenty faces whose vertices can be inscribed on the surface of a sphere or oval is contemplated as well. It is noted that as the number of faces of the polyhedron increases, the faces will more closely approximate the spherical or ellipsoidal surface on which the vertices of the polyhedron are inscribed.

Exemplary polyhedra include regular convex polyhedra such as platonic solids, regular nonconvex polyhedra such as Kepler-Poinsot polyhedra, semi-regular convex polyhedral such as Archimedean polyhedral, prisms, anti-prisms, Archimedean duals, quasiregular polyhedral, Johnson solids, pyramids, dipyramids, trapezohedra, compound polyhedra, stellated polyhedra, compounds of cubes, convex deltahedra, zonohedra, and the like.

In the tissue expander, the outer container and inner container independently comprise an elastomer. Thus, the outer container and inner container are the same or different elastomer material. Moreover, in the inner container, the reticulated frame and the projections are the same or different elastomer.

The tissue expander is made in a number of ways. In an embodiment, a process for making a tissue expander includes disposing a polymer on a mandrel and forming an inner container from the polymer on the mandrel. The inner container includes a reticulated framework comprising an interconnected network of struts and a plurality of projections disposed on and extending outwardly from the reticulated framework such that the struts having a thickness which is greater than a thickness of the projections. Here, the term "thickness" refers to a wall thickness of a strut or a wall thickness of the projection. According to the process, the polymer of the inner container is cured on the mandrel followed by removing the inner container from the mandrel and disposing the inner container in an outer container to make the tissue expander. The inner container is further processed by disposing an opening in the struts, the projections, or a combination thereof such that an interior of the inner container is in fluid communication with an interior of the outer container. The number of the openings is not limited. Further, the size of the opening is not particularly limited except that the opening is not so large as to compromise the structural integrity of the inner container so that the inner container remains flexible and self-expanding to its ordinarily open geometry such as when a compressive or stretching force is applied to the inner container and then relieved, i.e., removal of the force from the inner container.

The inner container is disposed in the outer container such that the inner container is free-floating in the outer container. That is, there is no point of attachment of the inner container to the outer container. Although the inner container is free to contact the outer container, the inner container is not tethered to the outer container. In some embodiments, the inner container is attached to the outer container. It is contemplated that such an attachment is a physical attachment (e.g., a tether, a clamp, a clip, a staple, a suture, and the like), a chemical attachment (e.g., an adhesive, a bond, and the like), and the like.

A filling tube is attached to the outer container. In some embodiments, a patch is disposed on the outer container or inner container to form a seal such that the filling tube is used to fill the outer container with a fluid with the outer container leaking. Since the inner and outer container are in fluid communication through the opening in the inner container.

Figure 49:
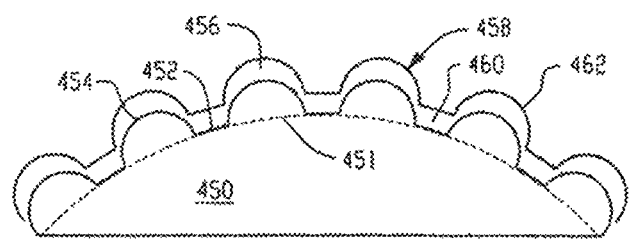
FIG. 49 shows a partial cross-section of an inner container disposed on a mandrel.
Figure 50:
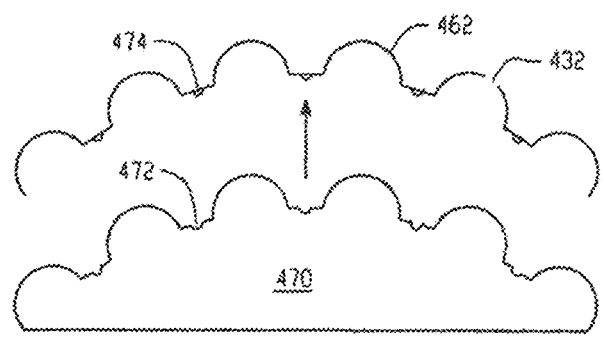
FIG. 50 shows a partial cross-section of an inner container and a mandrel used to form the inner container.
Figure 51:
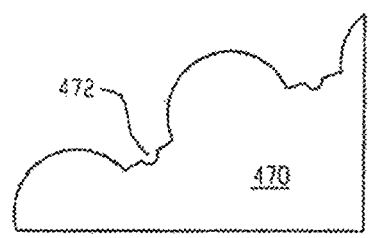
FIG. 51 shows an enlarged view of the mandrel shown in FIG. 50.

FIG. 49 shows a cross-section of an upper hemisphere of mandrel 450 that includes a surface having strut feature 452 and projection feature 454. Polymer 456 is disposed on mandrel 450 so that flexible inner container 458 is formed to have the shape of the surface of mandrel 450. In this manner, inner container 458 is formed with struts 460 and projections 462. As depicted in FIG. 50, to obtain struts 474 having a thicker wall thickness than the projections 462, mandrel 470 is used that has depressions 472 such that the polymer collects in depressions 472 to create struts 474 that are thicker than projections 462. An enlarged view of a portion of mandrel 470 appears in FIG. 51. Although the cross-sections of the upper hemispheres of the mandrels 450, 470 shown in FIGS. 49 and 50 are depicted as deriving from a spherical surface (as indicated by the dotted curve 451 in FIG. 49) that defines the position of the struts 460, 474 from which the projections 462 extend, the cross-sectional shape may differ from spherical such as ellipsoidal as well as the other shapes noted above for the inner container.

Once the inner container is formed, the inner container is removed from the mandrel. Such removal is accomplished by stretching the inner container over the mandrel to release the mandrel from the internal hollow space of the inner container. Here, it is contemplated that the inner container includes an orifice through which the mandrel is removed. In some embodiments, the mandrel is disintegrated or dissolved and particulates or remnants of the mandrel are removed from the inner container. Openings 432 (as shown in FIG. 50) are then made in the inner container such as by punching, cutting, laser forming, and the like. The inner container, which may or may not be free of the mandrel, is then inserted into an outer container. If the mandrel is still disposed in the inner container after the inner container is placed into the outer container, the mandrel is removed after disposing the inner container in the outer container.

Figure 52:
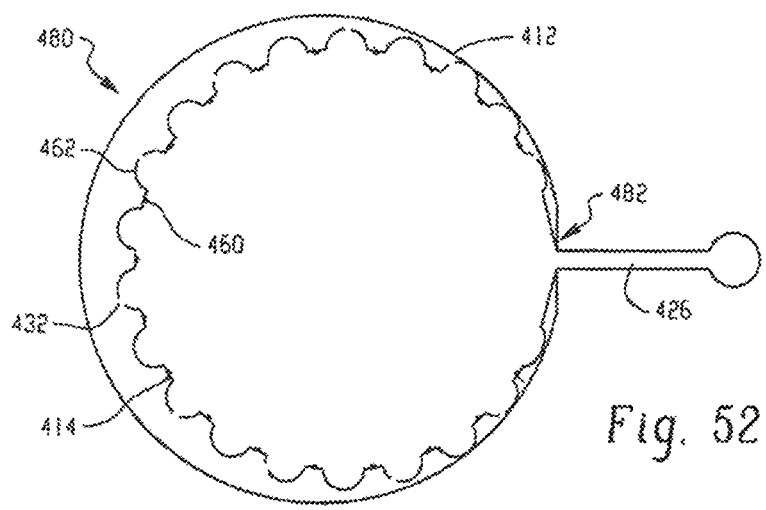
FIG. 52 shows a cross section of a tissue expander.

The resulting tissue expander 480 is, e.g., shown in FIG. 52 where inner container 414 having openings 432 is disposed in outer container 412 and attached by adhering inner container 414 to outer container 412 at point of attachment 482. Filling tube 426 is attached to outer container 412 for filling inner container 414 and outer container 412 with a fluid. In this embodiment, struts 460 of inner container 414 are thicker than projections 462.

Figure 53:
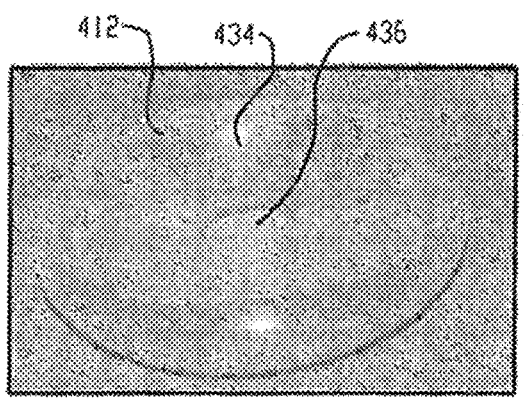
FIG. 53 shows a photograph of a posterior surface of an outer container.
Figure 54:
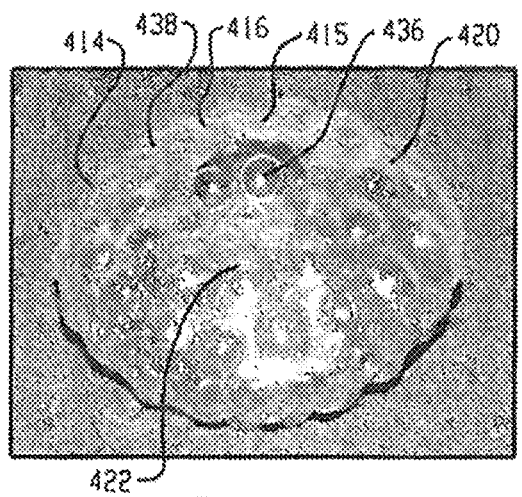
FIG. 54 shows a photograph of a posterior surface of an inner container.

FIG. 53 shows a posterior view of outer container 412 that has posterior surface 434 and orifice 436. Likewise, FIG. 54 shows a posterior view of inner container 414 that includes reticulated frame 415 of struts 416. Projections 420 are disposed on struts 416 and have openings 420. Orifice 436 is included in posterior surface 438 of inner 414 container to accommodate removal of the mandrel after formation of inner container 414 on the mandrel. Inner container 414 is disposed in outer container 412 through orifice 436 of outer container 412.

Figure 55:
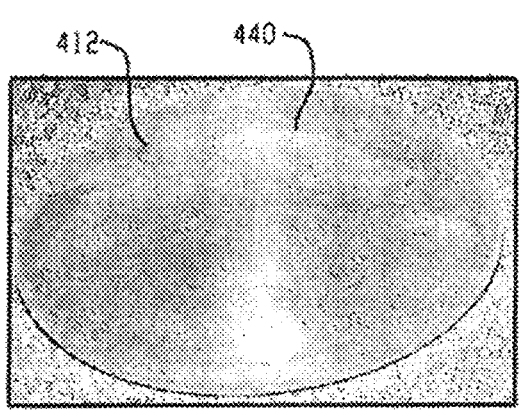
FIG. 55 shows a photograph of an anterior surface of the outer container shown in FIG. 49.
Figure 56:
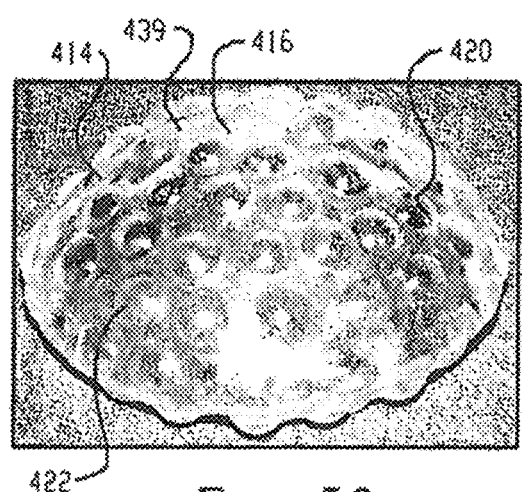
FIG. 56 shows a photograph of an anterior surface of the inner container shown in FIG. 50.

Anterior views of the outer container 412 and inner container 414 are respectively shown in FIGS. 55 and 56. Anterior surface 440 and posterior surface 434 of outer container 412 are smooth and non-corrugated. In some embodiments, anterior surface 440 or posterior surface 434 is rough or has surface corrugation, in either a regular or an irregular pattern. Anterior surface 439 of inner container 414 is similar to posterior surface 438 in that it also includes struts 416, projections 420, and optionally openings 422.

Figure 57:
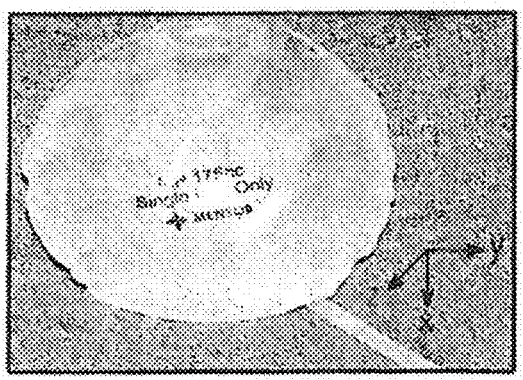
FIG. 57 shows a photograph of a tissue expander in a horizontal configuration without fluid in the outer container or inner container.
Figure 58:
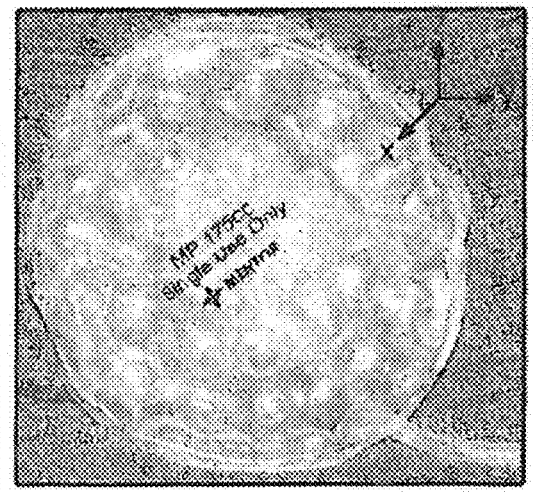
FIG. 58 shows a photograph of the tissue expander shown FIG. 53 in a vertical configuration and without fluid in the outer container or inner container.

The tissue expander herein has numerous advantageous or beneficial properties. The tissue expander after implantation in tissue has a long lifetime. Moreover, it is non-rigid, flexible, yet durable and rugged so that it withstands repeated movement, jostling, compression, and stretching. The inner container baffles fluid mobility and motion in the tissue expander so that it feels like normal, healthy tissue, including human breast tissue. Moreover, the inner container maintains its shape and supports the outer container so that tissue expander does not experience contortions in shape that are a function of gravity. More specifically, as shown in FIG. 57, when the tissue expander is placed on a flat surface such that is unfilled with a fluid and evacuated (containing little or no residual gas such as air), the tissue expander has an oblate spheroid shape. The mutually orthogonal x, y, and z axes are labeled according in FIG. 57 such that the x-y plane is coincident with the surface of the table, which is coplanar with the earth's surface (referred to as a "horizontal position"). Tilting the underlying surface by 60° (referred to as an "inclined position"), the tissue expander maintains nearly the same oblate shape as in FIG. 58.

Figure 59:
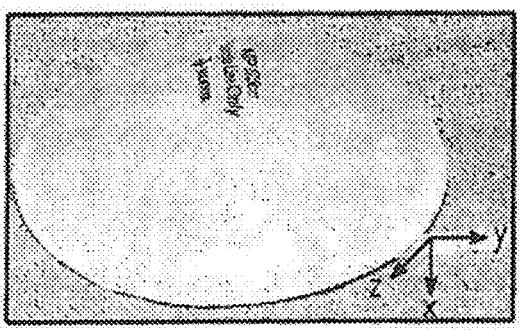
FIG. 59 shows a photograph of the tissue expander shown in FIG. 53 in a horizontal configuration with the outer container and inner container partially filled with fluid.
Figure 60:
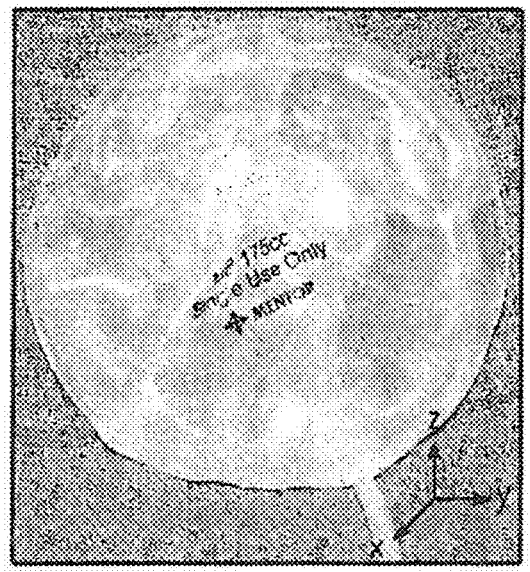
FIG. 60 shows a photograph of the tissue expander shown FIG. 53 in a vertical configuration with the outer container and inner container partially filled with fluid.
Figure 61:
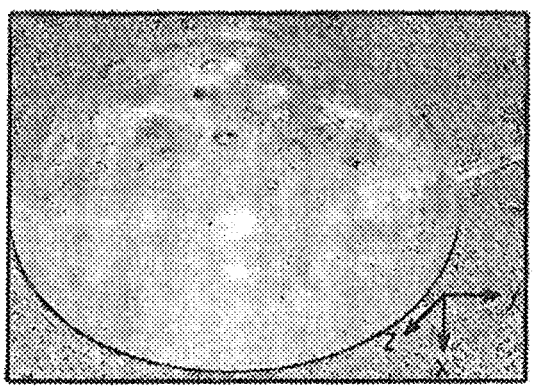
FIG. 61 shows a photograph of the tissue expander shown in FIG. 53 in a horizontal configuration with the outer container and inner container fully filled with fluid.
Figure 62:
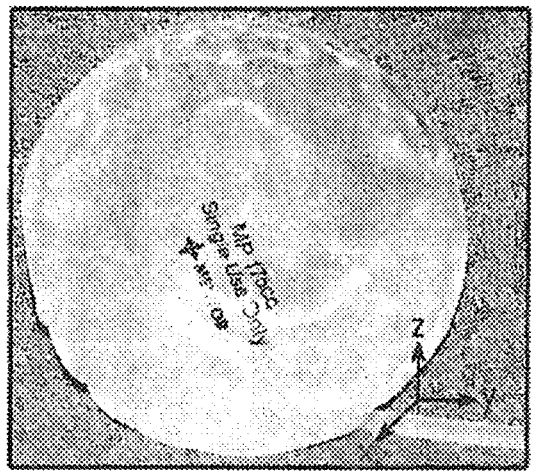
FIG. 62 shows a photograph of the tissue expander shown in FIG. 53 in a vertical configuration with the outer container and inner container fully filled with fluid.
Figure 63:
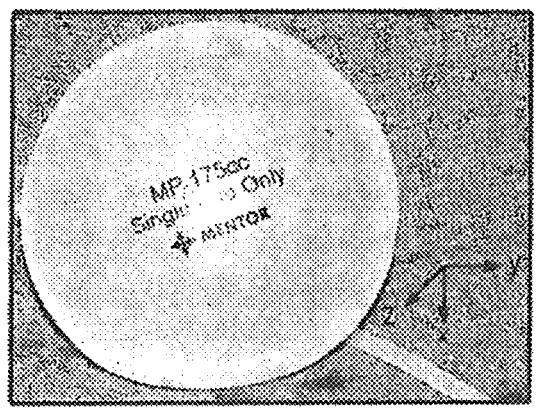
FIG. 63 shows a photograph of the tissue expander shown in FIG. 53 in a horizontal configuration with the outer container and inner container over filled with fluid.
Figure 64:
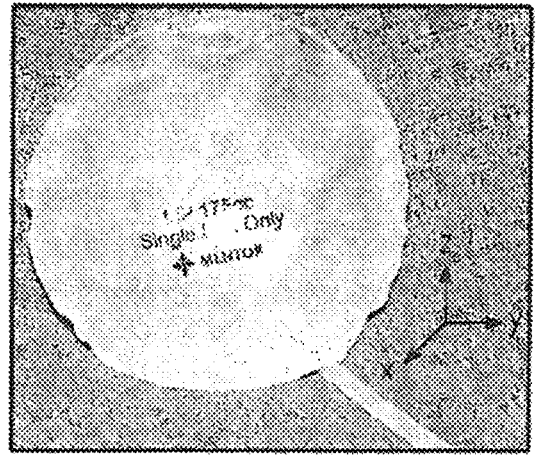
FIG. 64 shows a photograph of the tissue expander shown in FIG. 53 in a vertical configuration with the outer container and inner container over filled with fluid.

Upon partially filling the tissue expander to 75% of its full volume, the tissue expander maintains an oblate shape in the horizontal and inclined positions as shown respectively in FIGS. 59 and 60. It should be noted that the outer container does not fold or contort to a greatly different shape in the inclined position as compared with the horizontal position. As shown respectively in FIGS. 61 and 62, when the tissue expander is filled to its full volume, the expander also maintains its shape in the horizontal and inclined position. Advantageously, the outer container does not ripple, fold, or scallop. Similarly, as shown in FIGS. 63 and 64, when the tissue expander is overfilled to 120% of its full volume, the tissue expander further maintains its shape in the horizontal and inclined position without the outer container rippling, folding, or scalloping. Thus, regardless of the amount of fluid disposed in the tissue expander, the tissue expander maintains its shape in the horizontal and inclined positions. As such, the tissue expander is controlled to obtain a selected size without decreasing its aesthetic appearance or function due to surface or shape abnormalities or contortions.

Figure 65:
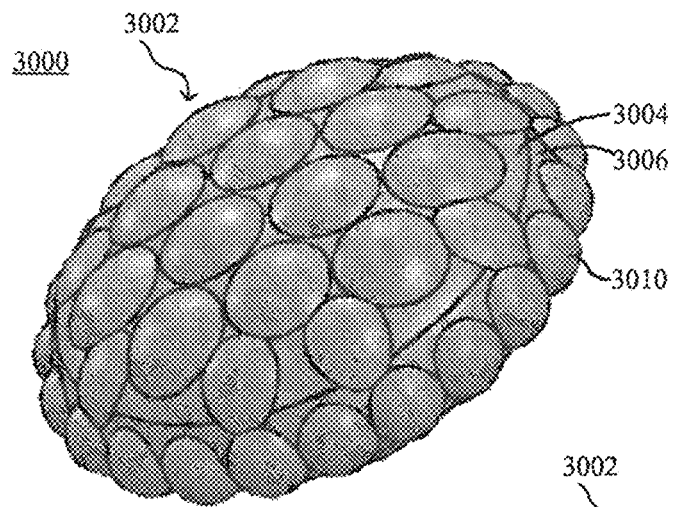
FIG. 65 shows a perspective view of an outer container.
Figure 66:
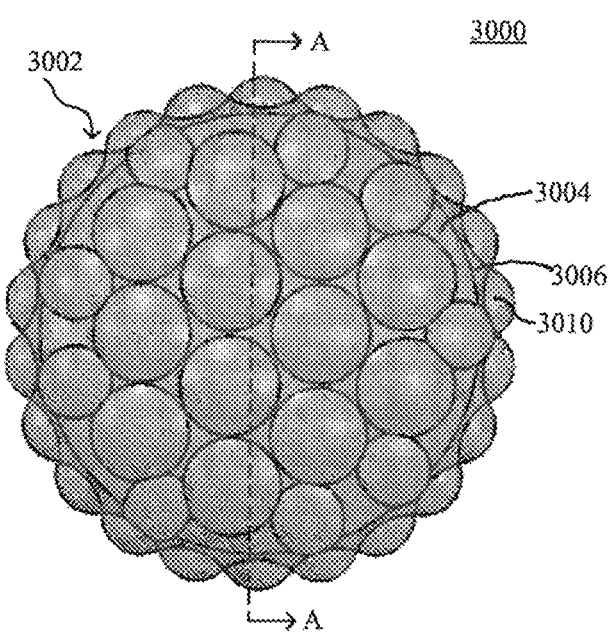
FIG. 66 shows a top view of the outer container shown in FIG. 65.
Figure 67:
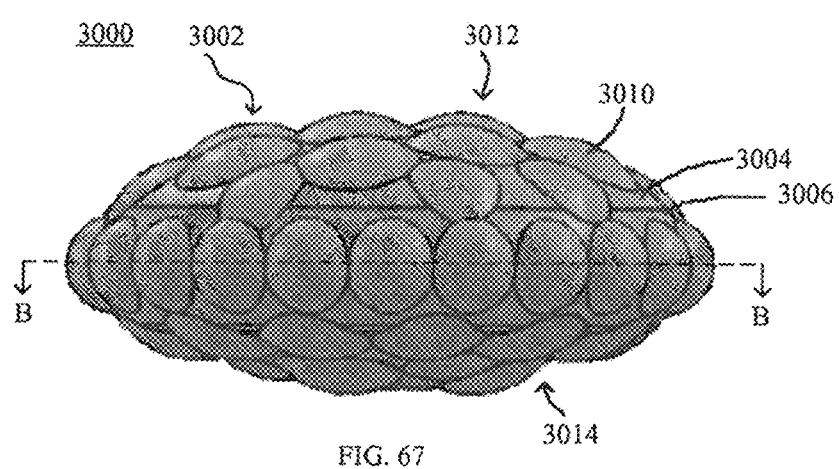
FIG. 67 shows a side view of the outer container shown in FIG. 65.

According to an embodiment, as shown in FIG. 65 (perspective view), FIG. 66 (top view of anterior side), and FIG. 67 (side view indicating anterior surface 3012 and posterior surface 3014), implant 3000 includes outer container 3002. Outer container 3002 has reticulated frame 3004. Reticulated frame 3004 includes a plurality of struts 3006 that interconnect, and in some embodiments, form a continuous network. Struts 3006 surround void (not shown but see, e.g., FIGS. 47 and 48 for exemplary voids) such that void is surrounded by struts 3006 in reticulated frame 3004. Projection 3010 connected to struts 3006 covers void. Projection 3010 is directly connected to struts 3006 to form a unitary item. Implant 3000 optionally includes a filling tube (not shown) or filling valve (not shown) for disposal of fluid in outer container 3002. The valve can be disposed through outer container 3002 and can be any of the valves previously discussed and provides a path by which the filling tube is disposed in outer container 3002 and can traverse a portion of the interior space of outer container 3002 to an exterior of outer container 3002 or can terminate at a surface of outer container 3002. In an embodiment, outer container 3002 is a temporary implant, e.g., a tissue expander, semi-permanent implant, or permanent implant (e.g., a breast implant). The filling tube can be hollow to transmit the fluid from a filling port (not shown) into outer container 3002.

Figure 68:
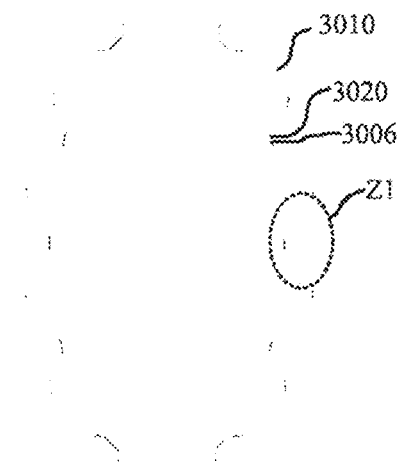
FIG. 68 shows a transverse cross-section along line A-A of the outer container shown in FIG. 66.
Figure 69:
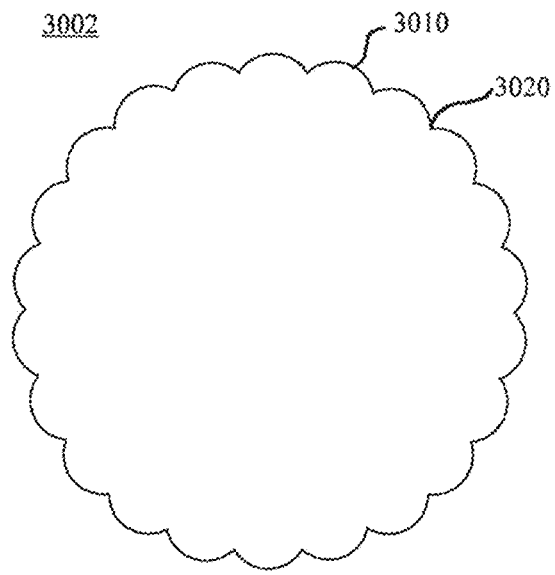
FIG. 69 shows a longitudinal cross-section along line B-B of the outer container shown in FIG. 67.
Figure 70:
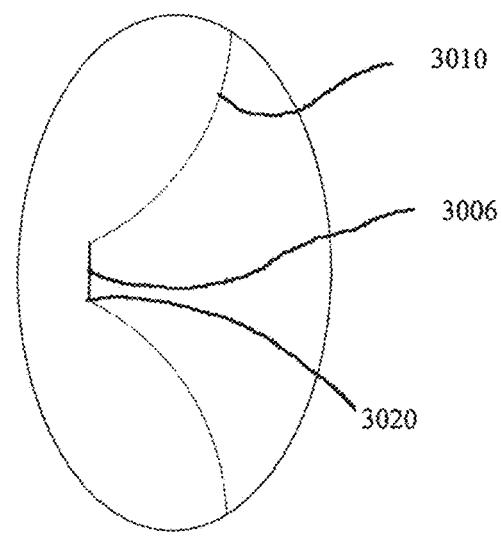
FIG. 70 shows an enlarged view of region "Z1" shown in FIG. 68.

FIG. 68 shows a transverse cross-section along line A-A through implant 3002 shown in FIG. 66. Here, outer container 3002 includes a plurality of projections 3010 separated by angular interface 3020 with struts 3006. An enlarged view of portion Z1 is shown in FIG. 70. FIG. 69 shows a longitudinal cross-section along line B-B through implant 3002 shown in FIG. 67. It is contemplated that projections 3010 and struts 3006 contact at angular interface 3020, which is a discontinuity from a smooth curve that transitions projections 3010 to struts 3006.

Figure 71A:
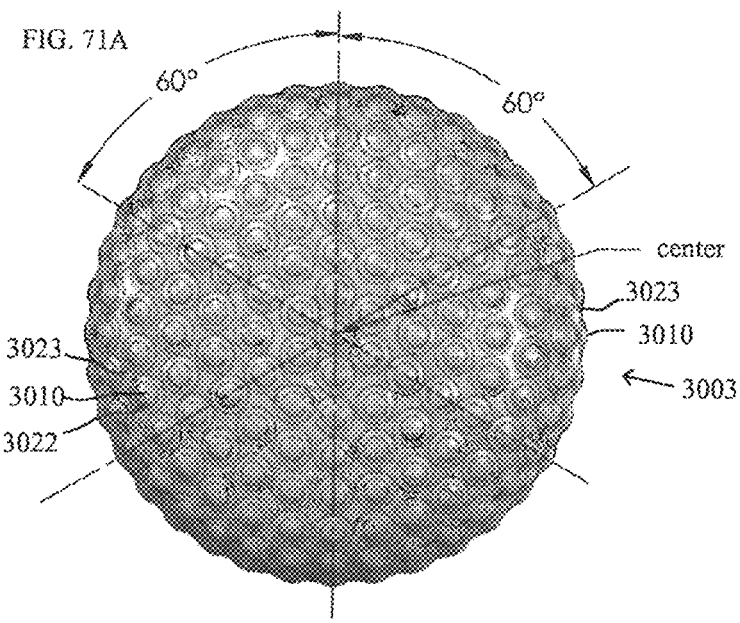
FIG. 71A shows an anterior views of a container.
Figure 71B:
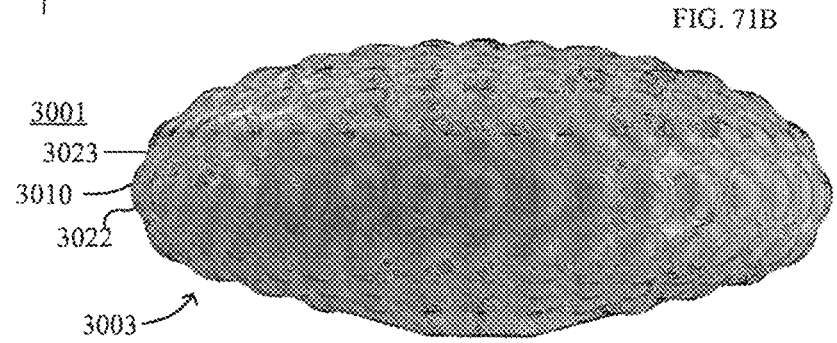
FIG. 71B shows a side view of the container shown in FIG. 71A.
Figure 71C:
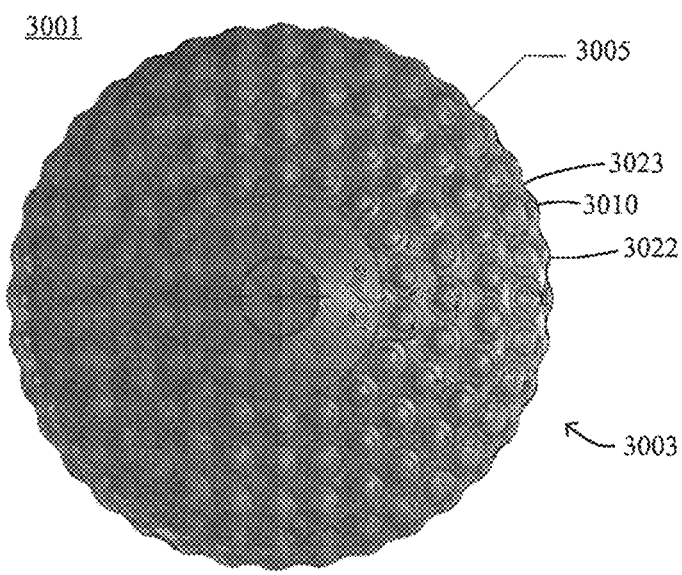
FIG. 71C shows a posterior view of the container shown in FIG. 71A.
Figure 72A:
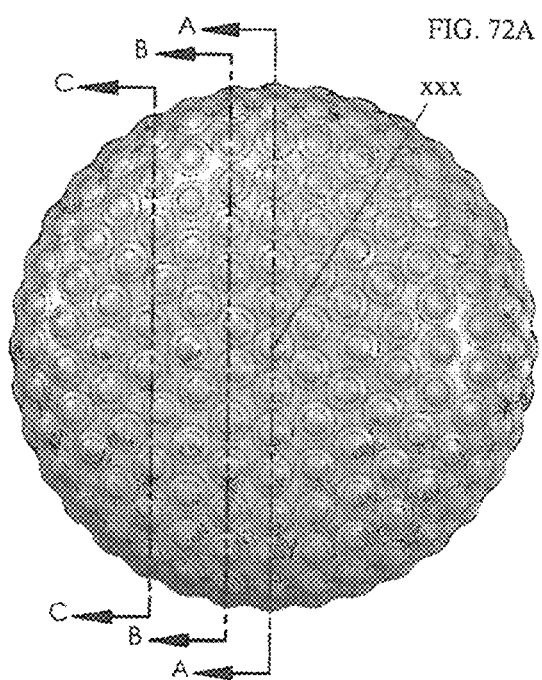
FIG. 72A shows the anterior view of the container shown in FIG. 71A labelled with lines A-A, B-B, and C-C.
Figure 72B:
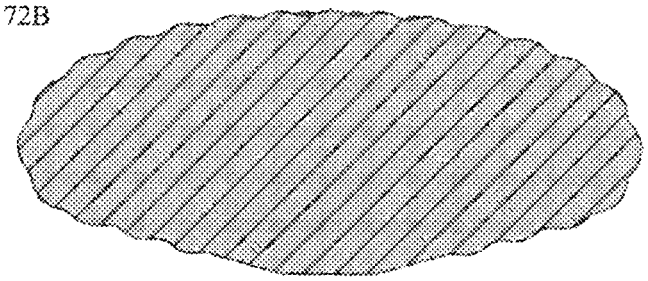
FIG. 72B shows a cross-section along line A-A of the container shown in FIG. 72A.
Figure 72C:
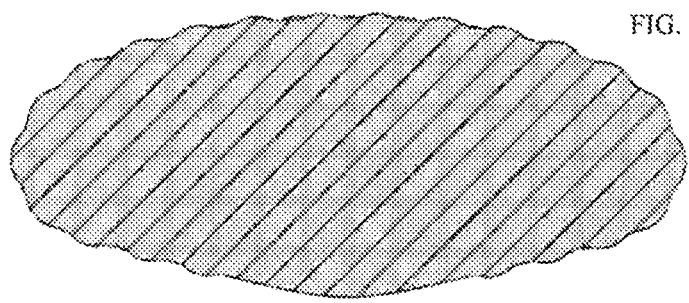
FIG. 72C shows a cross-section along line B-B of the container shown in FIG. 72A.
Figure 72D:
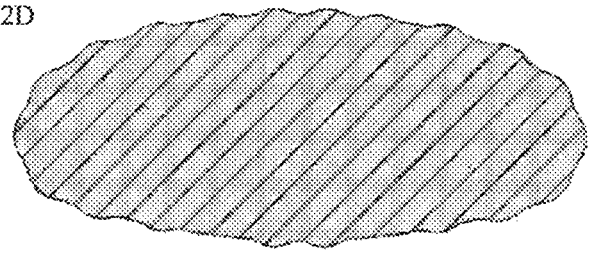
FIG. 72D shows a cross-section along line C-C of the container shown in FIG. 72A.
Figure 73A:
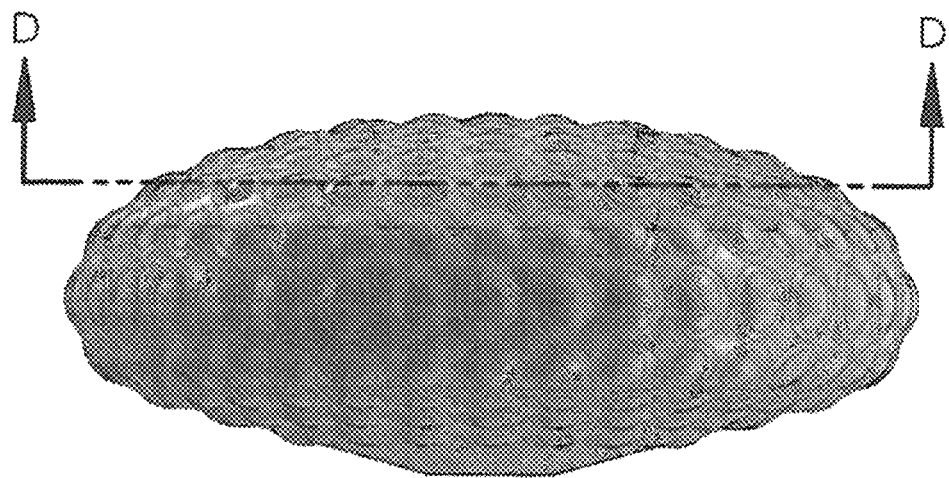
FIG. 73A shows the side view of the container shown in FIG. 71B labelled with line D-D.
Figure 73B:
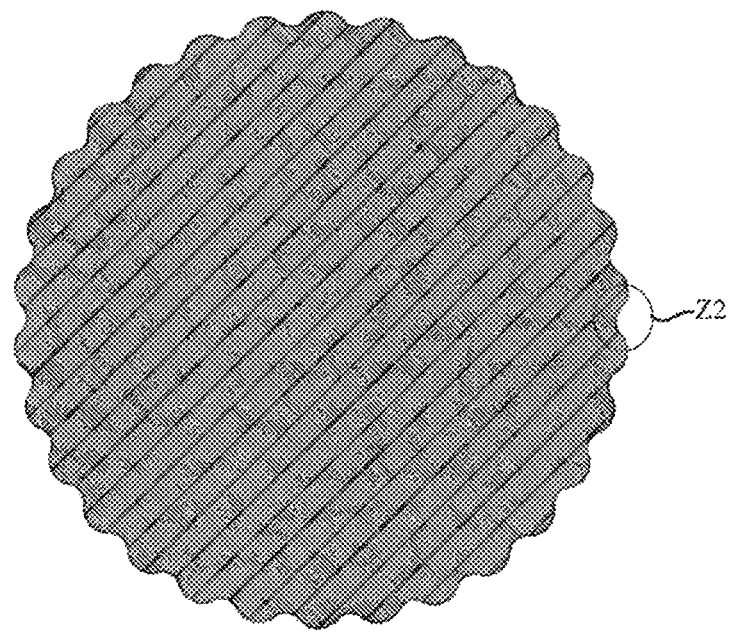
FIG. 73B shows a cross-section along line D-D of the container shown in FIG. 73A.
Figure 74:
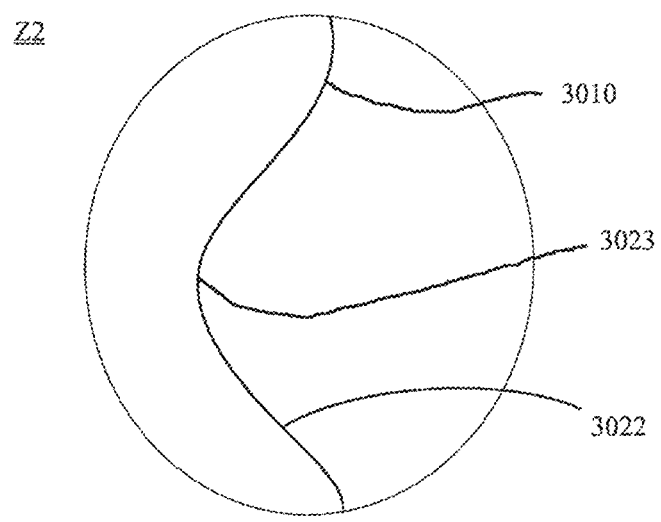
FIG. 74 shows an enlarged view of region "Z2" shown in FIG. 73B.

According to an alternative embodiment shown in FIG. 71A (anterior top view of implant 3001), 71B (side view of implant 3001), 71C (posterior view of implant 3001), 72A (anterior view of implant 3001), 72B (transverse cross-section along line A-A of implant 3001), 72C (transverse cross-section along line B-B of implant 3001), 72D (transverse cross-section along line C-C of implant 3001), 73A (side view of implant 3001), 73B (longitudinal cross-section along line D-D of implant 3001), and 74 (enlarged view of portion Z2 of implant 3001), implant 3001 includes sinusoidal container 3003 having smooth interface 3022 interposed between and to interconnect and transition between projection 3010 and trough 3023. In this manner, smooth interface 3022 smoothly connects projections 3010 to troughs 3023 without a discontinuity (e.g., that could be exhibited by angular interface 3020 in another embodiment as shown in FIG. 70). As shown in FIG. 73B, an enlarged view of portion Z2 shown in FIG. 74 indicates presence of a smooth transition between projections 3010 and troughs 3023 provided by smooth interface 3022. In this manner, the cross-sections of sinusoidal container 3003 shown, e.g., in FIGS. 72C, 72C, 72D, and 73B are meant to indicate that a cross-sectional shape of sinusoidal container 3003 has a surface that has periodically spaced projections 3010 spaced apart by troughs 3023 and having smooth interface 3022 to provide a sinusoidally contoured outer surface of sinusoidal container 3003. Moreover, a complete surface (anterior surface, dorsal surface, and side surface) is sinusoidally contoured such that sinusoidal container 3003 has a three-dimensional sinusoidal shape. That is, any cross-section taken along cut through implant 3001 has a sinusoidal boundary defined by the surface of the sinusoidal container 3003. In an embodiment, sinusoidal container 3003 includes angular interface 3020, smooth interface 3022, or a combination thereof.

In a certain embodiment, sinusoidal container 3003 includes a patch 3005 (shown in FIG. 71C) to seal sinusoidal container 3003 from leaking a fluid disposed therein. Here, sinusoidal container 3003 can include a filling tube or valve for disposal of fluid therein and to provide fluid communication between an interior of sinusoidal container 3003 and an external source of fluid.

According to an embodiment, implant 3001 includes a plurality of sinusoidal containers 3003. Here, a first sinusoidal container 3003 is arranged as an outer-most container and a second sinusoidal container 3003 is disposed in the first sinusoidal container 3003 such that the first and second sinusoidal containers 3003 are nested with the second sinusoidal container 3003 being an inner-most container with respect to the first sinusoidal container 3003. In a certain embodiment, an implant includes a plurality of containers (e.g., any of the containers herein) such that a first container (any container herein) is disposed as an outer-most container, and disposed in the first container is a second container (e.g., any of the containers or members herein, or more than one such second container, wherein each second container is a same or different type of container). Accordingly, this implant can include any container and any members or semi-shells, in any quantity and geometric arrangement, including nested arrangements or non-nested arrangements of internal members, internal containers, internal semi-shells, and the like.

According to an embodiment, a pitch of projections 3010 (i.e., spacing between adjacent projections) is selected to achieve above-discussed properties such as no rippling, no folding, or no scalloping of implant 3002. In an embodiment, the pitch is regular so that adjacent projections 3010 are evenly spaced on outer container 3002. In a certain embodiment, the pitch is irregular so that adjacent projections 3010 are not evenly spaced on outer container 3002. The pitch can be, e.g., from 15 mm to 40 mm. A shape of projection 3010 can approximate a portion of a sphere (e.g., can be hemispherical, or some other fraction of a sphere), oval, and the like. An outer diameter of projection 3010 can be, e.g., from 0.5 cm to 3 cm, specifically 1 cm to 2 cm. In an embodiment, the shape, size, and pitch of projections 3010 are selected so that outer container 3010 emulates normal, healthy human breast tissue that has surface contours (such as valleys) that mimic biological lobules when implanted in human tissue.

Figure 75:
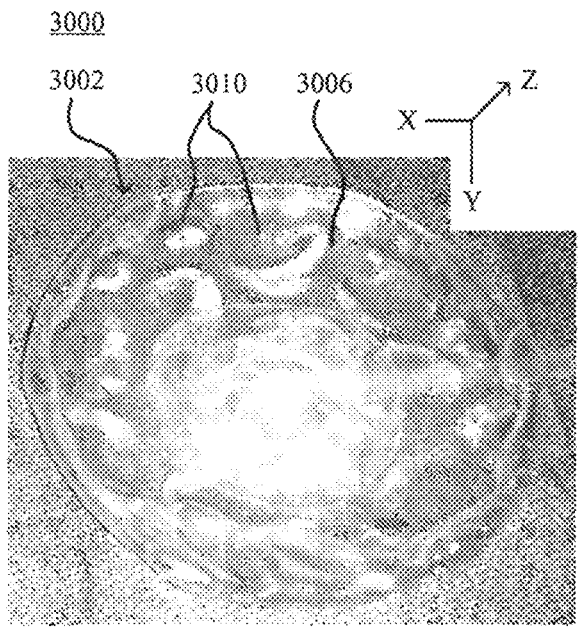
FIG. 75 shows a photograph of an outer container according to an embodiment in a horizontal configuration without fluid disposed in the outer container.

Implant 3000 includes outer container 3002 that maintains a shape and supports implant 3000 so that implant 3000 does not experience contortions in shape due to gravity. More specifically, as shown in FIG. 75, when implant 3000 is placed on a flat surface, not filled with a fluid (i.e., evacuated to contain little or no residual gas such as air or a liquid), implant 3000 has an oblate spheroid shape. The mutually orthogonal x, y, and z axes are labeled according to FIG. 75 such that the x-y plane is parallel with a surface of the table, which is coplanar with the earth's surface (referred to as a "horizontal position"). Tilting the surface of the table by 60° (referred to as an "inclined position" or "vertical position"), implant 3000 maintains a substantially same oblate shape as shown in in FIG. 77. That is, it should be appreciated that, in the inclined position, outer container 3002 maintains a flat, oblate shape that does not exhibit folding or any different surface morphological feature than when outer container 3002 is in the horizontal position.

Figure 76:
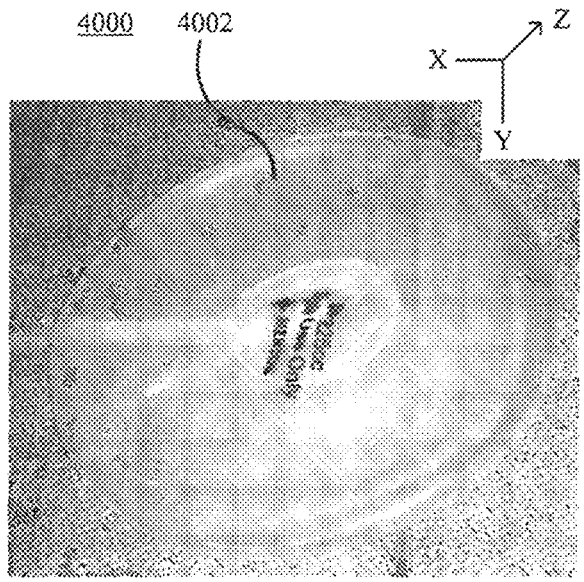
FIG. 76 shows a photograph of a conventional implant in a horizontal configuration without fluid disposed in the conventional implant.
Figure 77:
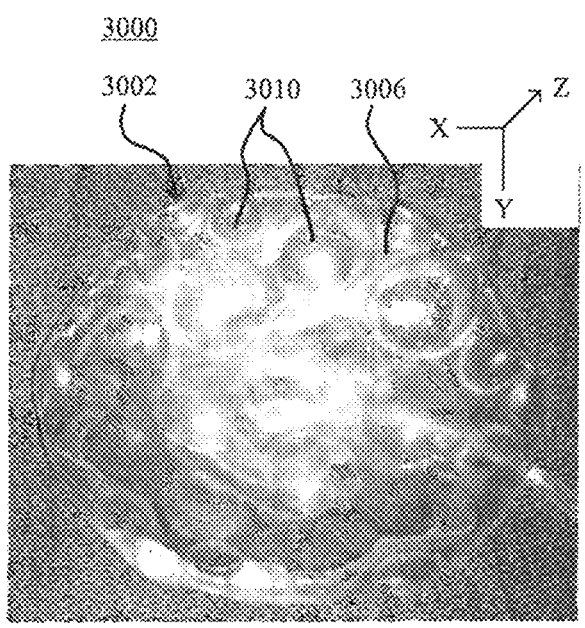
FIG. 77 shows a photograph of the outer container shown FIG. 75 in a vertical configuration without fluid disposed in the outer container.
Figure 78:
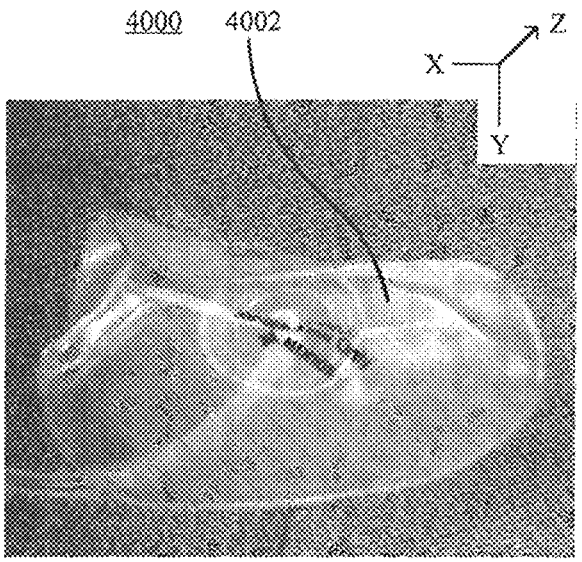
FIG. 78 shows a photograph of the conventional implant shown in FIG. 76 in a vertical configuration without fluid disposed in the conventional implant.

For comparison to the outer container 3002, conventional implant 4000 is shown in FIG. 76. Conventional implant 4000 includes smooth surface 4002 and is hollow. Here, conventional implant 4000 also does not have a fluid disposed therein and is held in a horizontal position. Similarly, FIG. 78 shows conventional implant 4000 in an inclined position. In the inclined position, conventional implant 4000 exhibits a modification to its surface morphology, particularly, conventional implant 4000 becomes folded when in an inclined position as compared to the horizontal position where conventional implant 4000 was flat and not folded.

Figure 79:
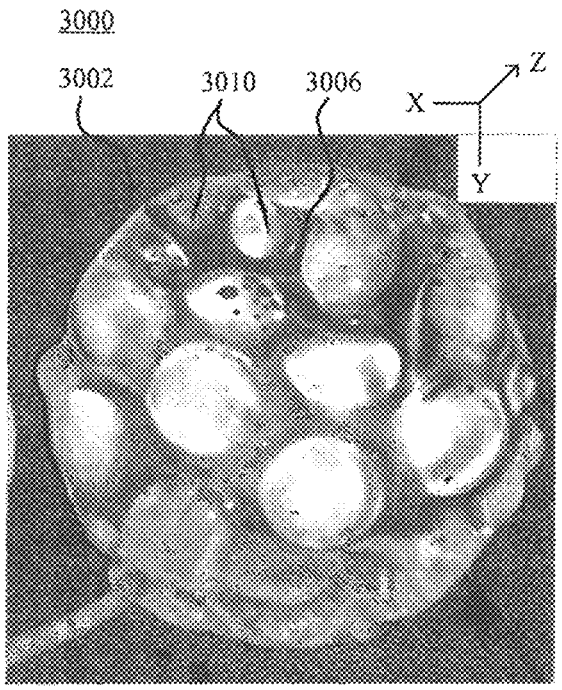
FIG. 79 shows a photograph of the outer container shown in FIG. 75 in a horizontal configuration with the outer container partially filled with fluid.
Figure 80:
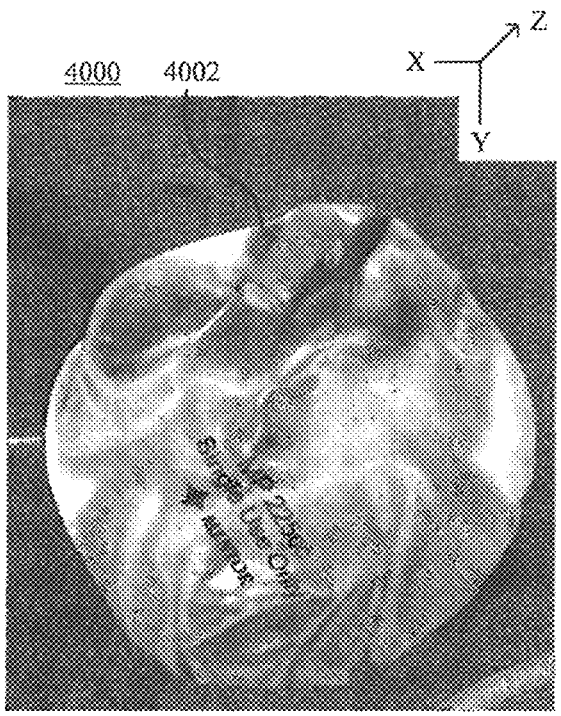
FIG. 80 shows a photograph of the conventional implant shown in FIG. 76 in a horizontal configuration with the conventional implant partially filled with fluid.
Figure 81:
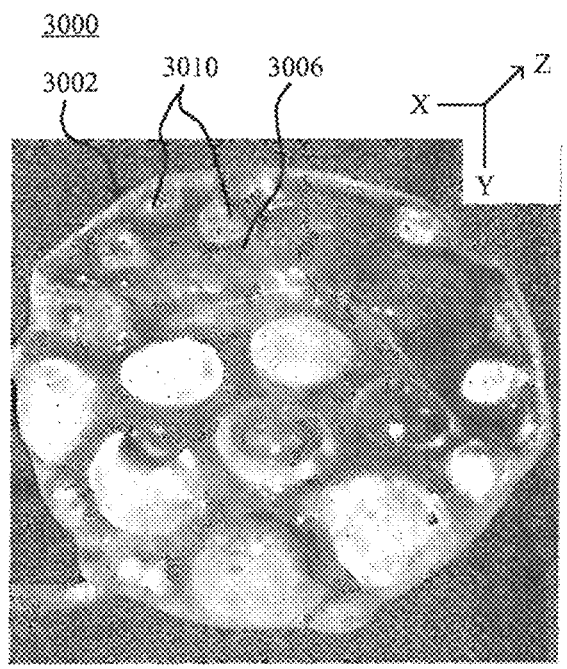
FIG. 81 shows a photograph of the outer container shown FIG. 75 in a vertical configuration with the outer container partially filled with fluid.
Figure 82:
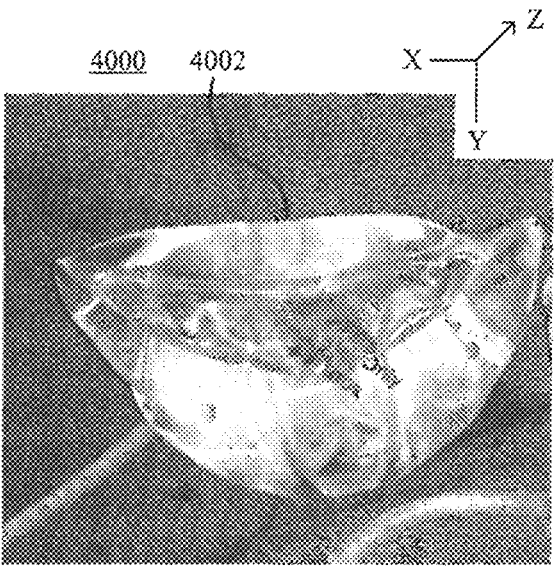
FIG. 82 shows a photograph of the conventional implant shown in FIG. 76 in a vertical configuration with the conventional implant partially filled with fluid.

Upon partially filling implant 3000 having outer container 3002 to 50% of its full volume, outer container 3002 maintains an oblate shape in the horizontal and inclined positions as shown respectively in FIGS. 79 and 81. It should be noted that outer container 3002 does not fold or contort to a greatly different shape in the inclined position as compared with the horizontal position. However, as shown in FIG. 80 (horizontal position) and FIG. 81 (inclined position), when conventional implant 4000 is filled with fluid to 50% of its full volume, conventional implant 4000 has surface wrinkles in the horizontal position (FIG. 80) and has surface wrinkles and folds in the inclined position (FIG. 82).

Figure 83:
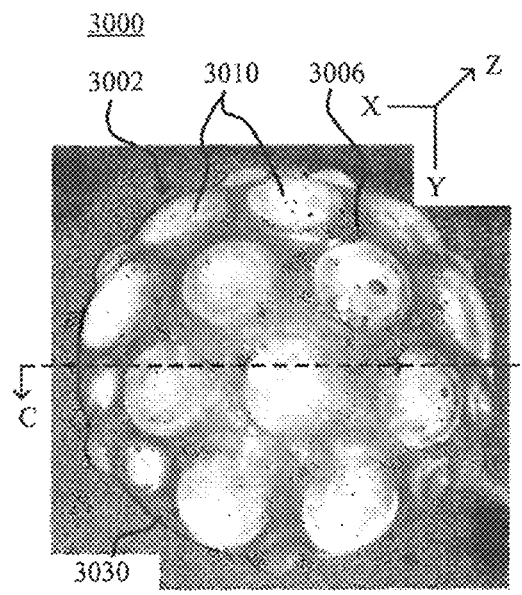
FIG. 83 shows a photograph of the outer container shown FIG. 24 in a horizontal configuration with the outer container fully filled with fluid.
Figure 85:
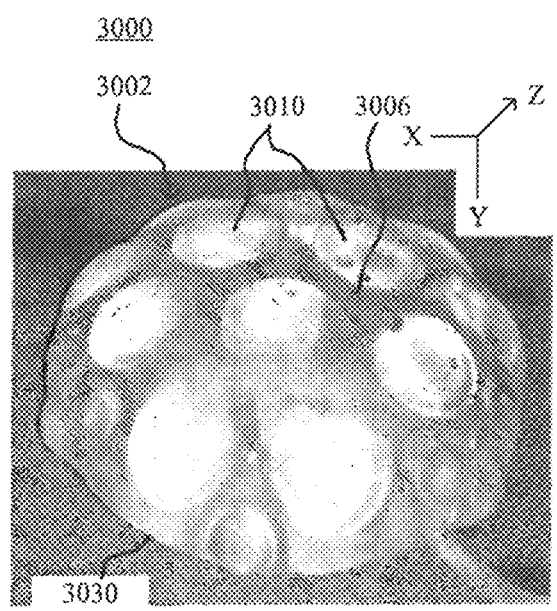
FIG. 85 shows a photograph of the outer container shown FIG. 75 in a vertical configuration with the outer container fully filled with fluid.

As shown respectively in FIGS. 83 and 85, when implant 3000 having outer container 3002 is filled to its full volume, outer container 3002 maintains its shape in the horizontal and inclined positions. Advantageously, outer container 3002 does not ripple, fold, or scallop. Thus, regardless of the amount of fluid disposed in implant 3000, outer container 3002 maintains its shape in the horizontal and inclined positions. As such, implant 3000 is controlled to obtain a selected size without decreasing its aesthetic appearance or function due to surface or shape abnormalities or contortions. Moreover, outer container 3002 includes smooth periphery 3030, which is clearly observed in a longitudinal cross-section long line C-C (of FIG. 83) implant 3000 shown in FIG. 87.

Figure 84:
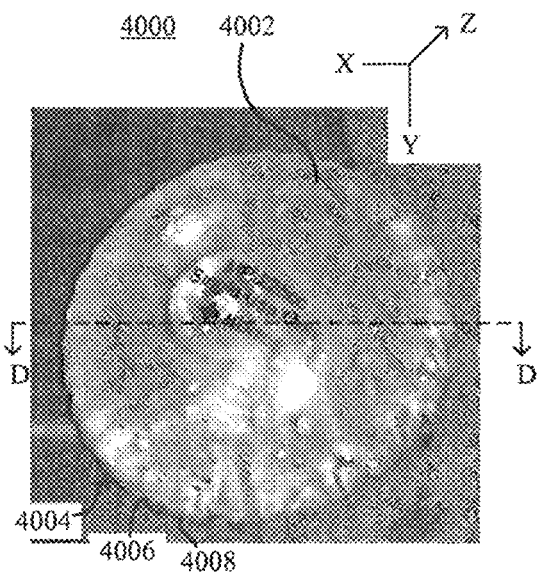
FIG. 84 shows a photograph of the conventional implant shown in FIG. 76 in a horizontal configuration with the conventional implant fully filled with fluid.
Figure 86:
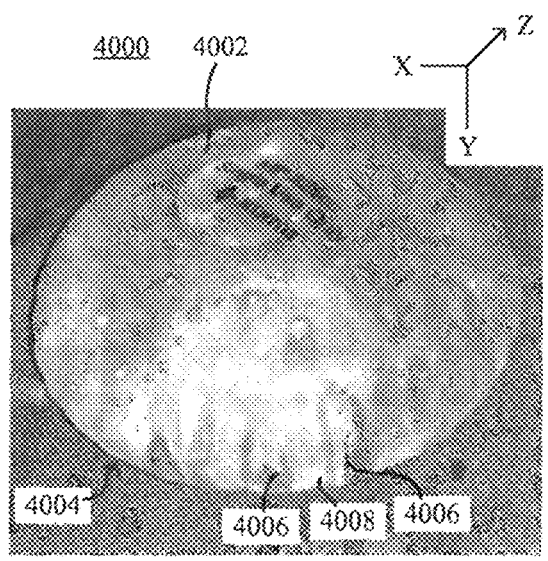
FIG. 86 shows a photograph of the conventional implant shown in FIG. 76 in a vertical configuration with the conventional implant fully filled with fluid.
Figure 87:
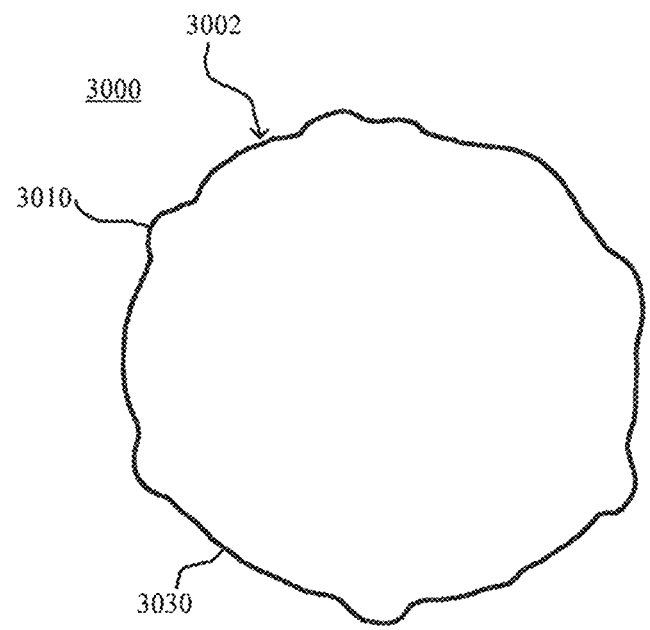
FIG. 87 shows a longitudinal cross-section along line C-C of the outer container shown in FIG. 85.
Figure 88:
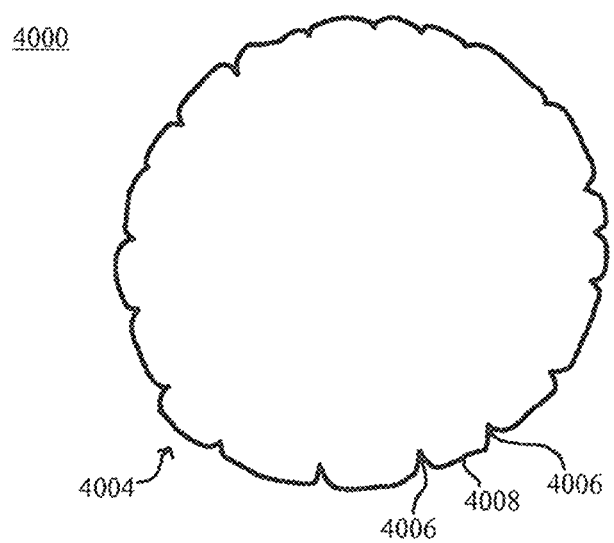
FIG. 88 shows a longitudinal cross-section along line D-D of the conventional implant shown in FIG. 86.

As shown respectively in FIGS. 84 and 86, when conventional implant 4000 having smooth surface 4002 is filled to its full volume, conventional implant 4000 does not maintain its shape in the horizontal and inclined positions. Instead, conventional implant 4000 exhibits a scalloped periphery 4004 and includes a plurality of alternating indentations 4006 and ridges 4008 that produce rippling, and scalloping to conventional implant 4000. That is, conventional implant 4000 includes scalloped periphery 4004 as shown in a longitudinal cross-section along line D-D (of FIG. 84) as shown in FIG. 88.

As used herein, the "full volume" of the tissue expander refers to the volume of the outer container without stretching the outer container. Thus, the tissue expander may be under-filled (filled with less than 100% of the full volume), over-filled (filled greater than 100% of the full volume), or fully filled.

Thus, the tissue expander is useful as an implantable device. According to an embodiment, a method for expanding tissue includes disposing the tissue expander in tissue and filling the tissue expander with a fluid to expand the tissue. The volume is selectable by the surgeon, and the amount of volume of the fluid (and thus size of the tissue expander) is adjustable by removal or introduction of fluid. Additionally, the tissue expander is disposed between muscle and skin. In some embodiments, the tissue expander is disposed below muscle such as between muscle and bone tissue. Regardless of location, the tissue expander is flexible and is configured to flex in response to a compressive force or a stretching force, and to return to an original shape in response to removal of the compressive force or the stretching force such that the outer container retains a primary shape, such as an anatomical shape, including a breast shape, a pectoral shape, a calf shape, and the like.

While one or more embodiments have been shown and described, modifications and substitutions may be made thereto without departing from the spirit and scope of the invention. Accordingly, it is to be understood that the present invention has been described by way of illustrations and not limitation. Embodiments herein can be used independently or can be combined.

All ranges disclosed herein are inclusive of the endpoints, and the endpoints are independently combinable with each other. The suffix "(s)" as used herein is intended to include both the singular and the plural of the term that it modifies, thereby including at least one of that term (e.g., the colorant(s) includes at least one colorant). "Optional" or "optionally" means that the subsequently described event or circumstance can or cannot occur, and that the description includes instances where the event occurs and instances where it does not. As used herein, "combination" is inclusive of blends, mixtures, alloys, reaction products, and the like. All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. "Or" means "and/or." It should further be noted that the terms "first," "second," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity). The conjunction "or" is used to link objects of a list or alternatives and is not disjunctive, rather the elements can be used separately or can be combined together under appropriate circumstances.

What is claimed:

1. An implant comprising:
   an outer container;
   an inner container; and
   at least one intermediate container positioned between the outer container and the inner container, wherein the at least one intermediate container comprises:
      a plurality of soft and flexible projections spaced around a perimeter of the at least one intermediate container, wherein the plurality of flexible projections expands and contracts as a fluid enters and exits from the at least one intermediate container;
      a plurality of troughs formed around the perimeter of the at least one intermediate container; and
      a plurality of smooth interfaces, wherein a smooth interface is interposed between a projection and an adjacent trough for the plurality of projections, troughs, and interfaces to provide a smooth continuous transition between adjacent projections and troughs.

2. The implant of claim 1, wherein the implant further comprises a valve disposed on the outer container, the valve comprising an internal path which is configured to communicate fluid into or out of an interior portion of the inner container and to selectively seal the implant.

3. The implant of claim 1, wherein the projections, the troughs, and the smooth interfaces are arranged on a surface of the at least one intermediate container, and an interior portion of the implant is a hollow cavity.

4. The implant of claim 1, wherein a longitudinal cross-section and a transverse cross-section of the at least one intermediate container have a shape that is a periodic wave across a surface of a wall that bounds an interior volume of the at least one intermediate container such that the at least one intermediate container has a three-dimensional shape.

5. The implant of claim 1, wherein the outer container is flexible and is configured to flex in response to a compressive force or a stretching force, and to return to an original shape in response to removal of the compressive force or the stretching force such that the outer container retains a primary shape.

6. The implant of claim 1, wherein the at least one intermediate container comprises an elastomer.

7. The implant of claim 1, further comprising a filling tube connected to the at least one container to communicate a fluid into the implant.

8. A method for expanding tissue, the method comprising:
   disposing the implant of claim 1 in tissue; and
   filling the implant with a fluid to expand the tissue.

9. The method of claim 8, wherein the implant is disposed between muscle and skin.

10. The method of claim 9, wherein the implant is flexible and is configured to flex in response to a compressive force or a stretching force, and to return to an original shape in response to removal of the compressive force or the stretching force such that the outer container retains a primary shape.

11. An implant comprising:
an outer container;
an inner container;
at least one intermediate container, wherein the at least one intermediate container comprises:
a plurality of projections spaced around a perimeter of the at least one intermediate container, wherein the plurality of projections expands and contracts as a fluid enters and exits from the at least one intermediate container;
a plurality of troughs spaced around the perimeter of the at least one intermediate container, wherein one trough of the plurality of troughs is positioned between adjacent projections; and
a plurality of smooth interfaces spaced around the perimeter of the at least one intermediate container, wherein one of the plurality smooth interfaces is interposed between a projection and an adjacent trough for the plurality of projections, troughs, and interfaces to provide a smooth continuous transition between adjacent projections and troughs in the at least one intermediate container.

12. An implant comprising:
an outer container;
an inner container;
a first at least one intermediate container, wherein the first intermediate container comprises:
a plurality of projections spaced around a perimeter of the first intermediate container, wherein the plurality of projections expands and contracts as a fluid enters and exits from the at first intermediate container;
a plurality of troughs spaced around the perimeter of the first intermediate container, wherein one trough of the plurality of troughs is positioned between adjacent projections;
a plurality of smooth interfaces spaced around the perimeter of the first intermediate container; and
a second intermediate container disposed in the first intermediate container, the second container comprising:
a plurality of second intermediate container projections spaced around a perimeter of the second intermediate container;
a plurality of second intermediate container troughs spaced around the perimeter of the second intermediate container wherein one second intermediate container trough of the plurality of second intermediate container troughs is positioned between adjacent second intermediate container projections; and
a plurality of second intermediate container smooth interfaces spaced around a perimeter of the second intermediate container.

* * * * *